(12) United States Patent
Hsu et al.

(10) Patent No.: US 9,303,117 B2
(45) Date of Patent: Apr. 5, 2016

(54) CHEMICALS AND THE SYNTHESIZING METHODS THEREOF

(71) Applicant: National Chiao Tung University, Hsinchu (TW)

(72) Inventors: Chain-Shu Hsu, Hsinchu (TW); Yen-Ju Cheng, Hsinchu (TW); Jhong-Sian Wu, Changhua County (TW); Chiu-Hsiang Chen, Taichung (TW); Huan-Hsuan Chang, Yilan County (TW); Yung-Lung Chen, Miaoli County (TW); Sheng-Wen Cheng, Taipei (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 14/753,379

(22) Filed: Jun. 29, 2015

(65) Prior Publication Data
US 2015/0299382 A1 Oct. 22, 2015

Related U.S. Application Data

(62) Division of application No. 14/092,025, filed on Nov. 27, 2013, now Pat. No. 9,096,716, which is a division of application No. 13/532,631, filed on Jun. 25, 2012, now Pat. No. 8,623,993.

(30) Foreign Application Priority Data

Mar. 8, 2012 (TW) .............................. 101107975 A

(51) Int. Cl.
| | |
|---|---|
| C08G 75/00 | (2006.01) |
| C08G 61/12 | (2006.01) |
| C07D 495/04 | (2006.01) |
| C07D 495/14 | (2006.01) |
| C07D 495/22 | (2006.01) |
| C08G 77/60 | (2006.01) |
| C08G 75/32 | (2006.01) |
| C08G 69/40 | (2006.01) |
| C08G 73/10 | (2006.01) |
| C08G 75/06 | (2006.01) |
| H01L 51/00 | (2006.01) |
| H01L 51/44 | (2006.01) |

(52) U.S. Cl.
CPC ............ *C08G 61/126* (2013.01); *C07D 495/04* (2013.01); *C07D 495/14* (2013.01); *C07D 495/22* (2013.01); *C08G 61/123* (2013.01); *C08G 61/124* (2013.01); *C08G 69/40* (2013.01); *C08G 73/1064* (2013.01); *C08G 75/06* (2013.01); *C08G 75/32* (2013.01); *C08G 77/60* (2013.01); *H01L 51/0036* (2013.01); *H01L 51/0043* (2013.01); *H01L 51/0044* (2013.01); *H01L 51/0094* (2013.01); *C08G 2261/12* (2013.01); *C08G 2261/124* (2013.01); *C08G 2261/1412* (2013.01); *C08G 2261/18* (2013.01); *C08G 2261/3223* (2013.01); *C08G 2261/3243* (2013.01); *C08G 2261/3246* (2013.01); *C08G 2261/3247* (2013.01); *C08G 2261/344* (2013.01); *C08G 2261/414* (2013.01); *C08G 2261/514* (2013.01); *C08G 2261/91* (2013.01); *H01L 51/44* (2013.01)

(58) Field of Classification Search
CPC ....................................................... C08G 77/60
USPC ................................................... 528/380, 377
See application file for complete search history.

(56) References Cited

U.S. PATENT DOCUMENTS

2003/0186079 A1   10/2003   Towns et al.

OTHER PUBLICATIONS

Wu et al., "Carbazole-Based Heptacyclic Arenes with Carbon, Silicon, and Nitrogen bridges: Synthesis, Molecular Properties and Photovoltaic Applications", (Prep. Pap. ACS, Div. Fuel Chem., 2012, 57 (1), 774, Mar. 25-29, 2012, San Diego, CA.
Wu et al., "Donor-Acceptor Polymers Based on Multi-Fused Heptacyclic Structures: Synthesis, Characterization and Photovoltaic Applications" (Chem. Commun., 2010, 46, 3259-3261).
Chen et al., "Donor-Acceptor Random Copolymers Based on a Ladder-Type Nonacyclic Unit: Synthesis, Characterization, and Photovoltaic Applications,"Macromolecules (2011) 44 (21): 8415-8424.
Cheng et al., "Ladder-Type Nonacyclic Structure Consisting of Alternate Thiophene and benzene Units for Efficient Conventional and Inverted Organic Photovoltaics," Chemistry of Materials (2011) 23 (22): 5068-5075.
Chang et al., "Combination of Molecular, Morphological, and Interfacial Engineering to Achieve Highly Efficient and Stable Plastic Solar Cells," Adv. Mater (2012) 24 (4): 549-553.
Wu et al., "Dithienocarbazole-Based Ladder-Type Heptacyclic Arenes with Silicon, Carbon, and Nitrogen Bridges: Synthesis, Molecular Properties, Field-Effect Transistors, and Photovoltaic Applications," Adv. Funct. Mater. (2012) 22 (8): 1711-1722.
Cheng et al., "Diindenothieno [2,3-b] Thiopene Arene for Efficient Organic Photovoltaics With an Extra High Open-Circuit Voltage of 1.14.," Chem. Commun. (2012) 48: 3203-3205.

*Primary Examiner* — Shane Fang
(74) *Attorney, Agent, or Firm* — Volpe and Koenig, P.C.

(57) ABSTRACT

A series of ladder-type multifused arenes (hexacyclic, heptacyclic and nonacyclic units) and the synthesizing methods thereof are provided. The ladder-type multifused arenes are copolymerized with various electron-deficient acceptor units to afford various p-type low-band gap conjugated copolymers.

2 Claims, No Drawings

CHEMICALS AND THE SYNTHESIZING METHODS THEREOF

This application is a divisional of U.S. patent application Ser. No. 14/092,025, filed on Nov. 27, 2013, which is a divisional of U.S. patent application Ser. No. 13/532,631, filed on Jun. 25, 2012, which issued on Jan. 7, 2014 as U.S. Pat. No. 8,623,993, which claims the benefit of Taiwan Patent Application No. 101107975, filed on Mar. 8, 2012 in the Taiwan Intellectual Property Office, the disclosures of which are all incorporated by reference as if fully set forth herein.

FIELD OF THE INVENTION

The present invention relates to a polymer monomer and the polymers thereof, and the synthetic method of the monomer and the polymers, wherein the polymers can serve as an active layer material of an organic polymer solar cell.

BACKGROUND OF THE INVENTION

In order to achieve the goal of the high efficiency organic polymer solar cell, it is a key point to use a good p-type conjugated polymer semiconductor material. Usually, the p-type conjugated polymer applied to the organic polymer solar cell should have the following properties: 1) a low-band gap (smaller than 1.7 eV) for having a strong and broad absorption spectrum to the scopes of the red light or the infrared ray in order to utilize the sunlight completely, 2) a high electron hole mobility (larger than $10^{-3}$ $cm^2V^{-1}S^{-1}$) for increasing the thickness of the active layer to strengthen the light collection and decreasing the serial resistors at the same time, and thus preventing from the electron hole recombination, 3) a high solubility for satisfying the demands of solvent wet process, and 4) a lower energy level (highest occupied molecular orbital, HOMO) for achieving a higher open circuit voltage, and the lowest unoccupied molecular orbital (LOMO) energy level must at least higher than the LUMO 0.3V of the n-type semiconductor material for forming the electron transition potential to facilitate the exciton separation.

SUMMARY OF THE INVENTION

The present invention relates to the chemical structures of the ladder-type multifused multi-electron donor materials and the synthetic method thereof, and to the p-type low-band gap conjugated polymer formed of the ladder-type multifused multi-electron donors and an electron-deficient acceptor, the synthetic method thereof and the application thereof in the field of the organic polymer solar cell.

In order to achieve the above purposes, the present invention provides a polymer, having a structure being one selected from a group consisting of:

Formula (I)

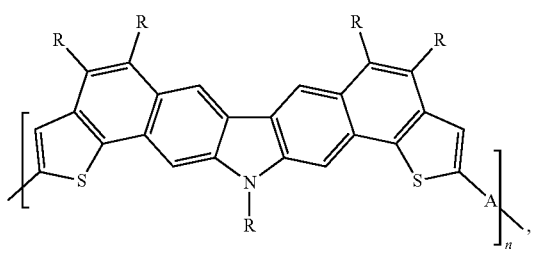

Formula (II)

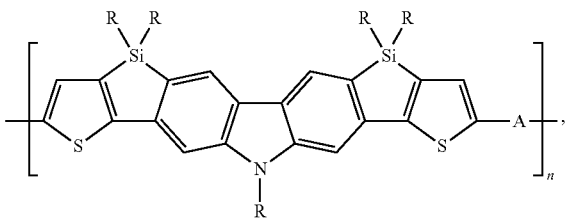

Formula (III)

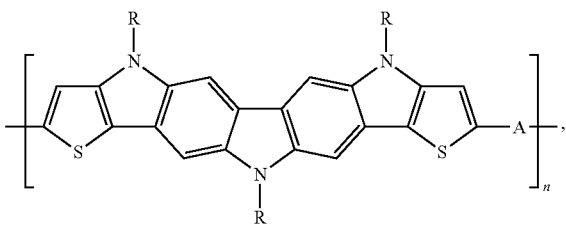

Formula (IV)

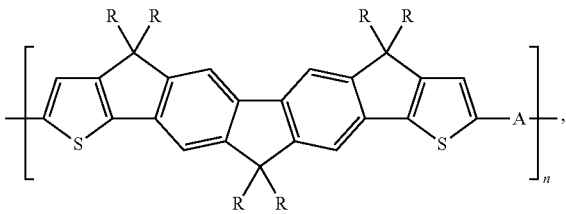

Formula (V)

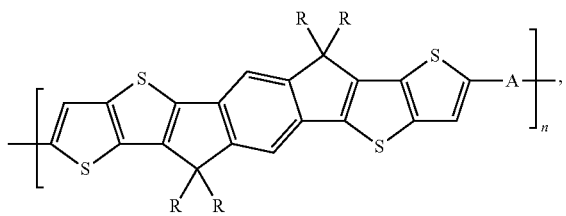

Formula (VI)

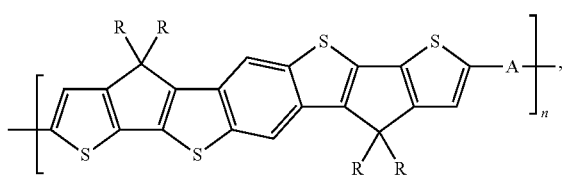

Formula (VII)

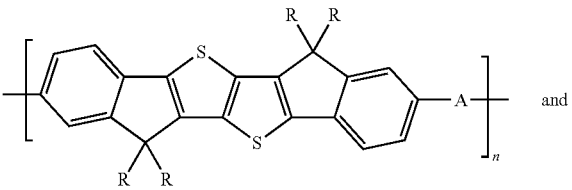

and

Formula (VIII)

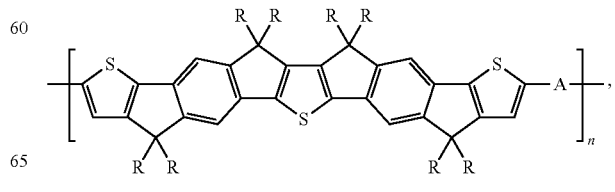

wherein A is an electron-deficient monomer, n is an integer larger than 2 and R is a side chain at least including a carbon atom.

In order to achieve the above purposes, the present invention also provides a polymer monomer having a structure being one selected from a group consisting of:

Formula (I)
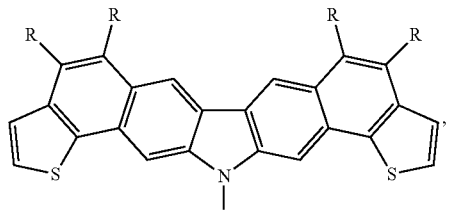

Formula (II)
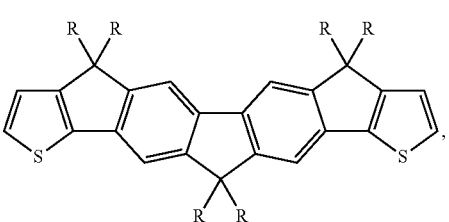

Formula (III)
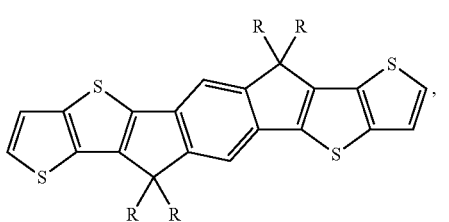

Formula (IV)
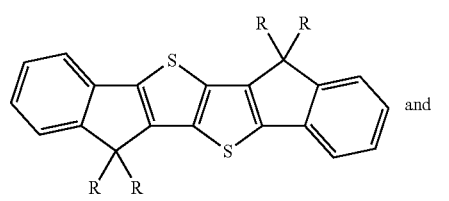

and

Formula (V)
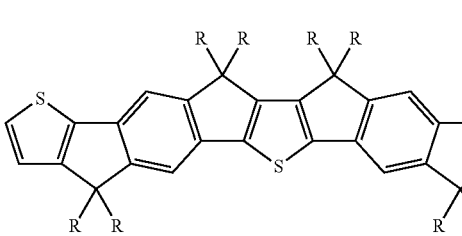

wherein R is a side chain at least including a carbon atom.

In order to achieve the above purposes, the present invention further provides a method of synthesizing a monomer, including steps of providing a compound having a structure being one of Formula (I)
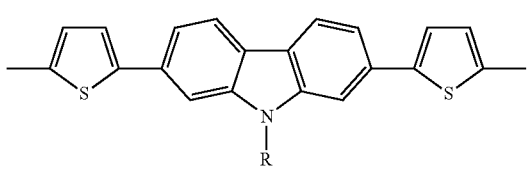

and

Formula (II)
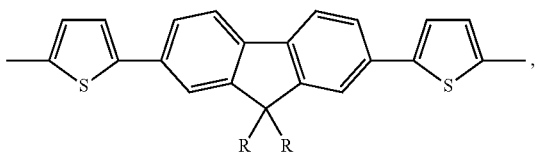

wherein R is a side chain at least including a carbon atom, and performing an annulation with the compound to cause the compound to form the monomer.

Other objects, advantages and efficacies of the present invention will be described in detail below taken from the preferred embodiments with reference to the accompanying drawings, in which:

DETAILED DESCRIPTION OF THE PREFERRED EMBODIMENT

The products and method of the present invention will be fully understood from the following embodiments and thereby being accomplished based thereon by one skilled in the art. However, the practice of the present application is not intended to limit to the following embodiments in its practice, and the skilled person can still conduct other embodiments according to the spirit of embodiments presented herein that belong to the scope of this invention.

The synthetic processes of the heptacyclic multielectron monomer Sn-DTBC are provided as follows.

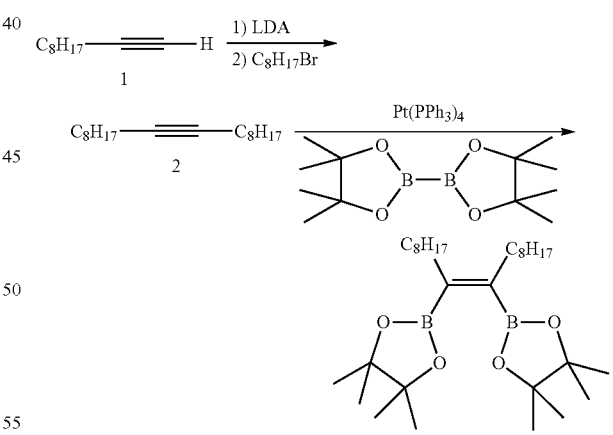

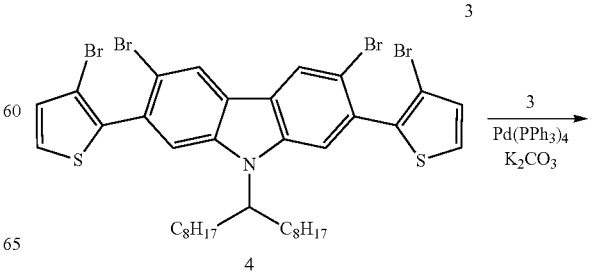

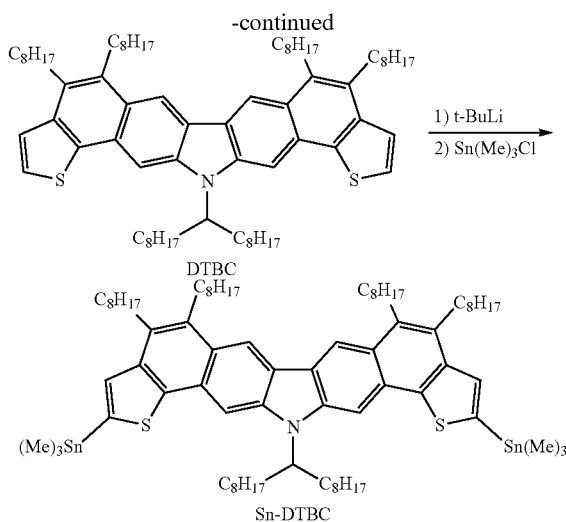

The Synthesis of the Compound 2:

The compound 1 (6.0 g, 43.4 mmol) is placed in a 250 mL double-necked flask under vacuum and to be baked therein for three times, 60 mL anhydrous tetrahydrofuran is added thereinto, and then the lithium diisopropylamide (2.0 M, 23.9 mL, 47.8 mmol) is slowly dropped thereinto under 0° C. for reacting for 1 hr. The mixture is returned to the room temperature after adding 1-bromooctane (8.8 g, 45.6 mmol), and being heated under 60° C. at reflux for 12 hrs. The reaction is terminated by adding water, and the organic solvent is removed under lowered pressure. The organic layer is collected by extracting with ether (50 mL×3) and pure water (50 mL), and the collected organic layer is dried over magnesium sulfate ($MgSO_4$). After removal of the organic solvent again under lowered pressure, the residue is removed by lowered pressure distillation at 150° C. Finally, the residue is purified by column chromatography on silica gel (using hexane as eluent) to give a colorless liquid 2 (2.7 g, 25%). $^1$H NMR ($CDCl_3$, 300 MHz, ppm): (t, J=6.6 Hz, 6H), 1.27-1.38 (m, 20H), 1.45-1.49 (m, 4H), 2.13 (t, J=6.9 Hz, 4H).

The Synthesis of the Compound 3:

The compound 2 (2.5 g, 9.98 mmol) and bis(pinacolato)diboron (2.3 g, 9.07 mmol) are placed in a 100 mL double-necked flask, and the $Pt(PPh_3)_4$ (339 mg, 0.27 mmol) is added into the double-necked flask in a glove box. After transferring the double-necked flask outside the glove box, 40 mL of DMF is added into the flask under nitrogen. After heating the stirring the mixture at 80° C. for 24 hrs, the organic layer is collected by extracting with ether (200 mL×3) and pure water (100 mL), the collected organic layer is dried over $MgSO_4$, and the organic solvent is removed under lowered pressure. Finally, the residue is purified by column chromatography on silica gel (ethyl acetate/hexane v/v=1/25 as eluent) to give a colorless liquid 3 (3.77 g, 75%). $^1$H NMR ($CDCl_3$, 300 MHz, ppm): (m, 6H), 1.21-1.31 (m, 48H), 2.16 (t, J=7.5 Hz, 4H).

The Synthesis of the DTBC Compound

The compound 3 (0.701 g, 1.39 mmol), the compound 4 (0.513 g, 0.579 mmol) and $K_2CO_3$ (0.96 g, 6.952 mmol) are placed in a 100 mL double-necked flask, and the $Pd(PPh_3)_4$ (67 mg, 0.058 mmol) is added into the double-necked flask in a glove box. After transferring the double-necked flask outside the glove box, 25 mL tetrahydrofuran pre-degassed with nitrogen and 1.2 mL pure water are added into the flask under nitrogen. After heating the mixture at 65° C. at reflux for 48 hrs, the organic solvent is removed therefrom under lowered pressure. The organic layer is collected by extracting with ether (100 mL×3) and pure water (150 mL), and the collected organic layer is dried over magnesium sulfate ($MgSO_4$). After removal of the organic solvent under lowered pressure, the residue is purified by column chromatography on silica gel (using hexane as eluent) to give a yellow sticky DTBC (0.312 g, 51%). $^1$H NMR ($CDCl_3$, 300 MHz, ppm): δ 0.73 (t, J=6.6 Hz, 6H), 0.90 (t, J=6.9 Hz, 12H), 1.08 (br, 18H), 1.22-1.52 (m, 42H), 1.64-1.78 (m, 8H), 1.82-1.94 (m, 4H), 1.98-2.06 (m, 2H), 2.48-2.58 (m, 2H), 3.12 (t, J=7.8 Hz, 4H), 3.33 (t, J=7.8 Hz, 4H), 4.70-4.80 (m, 1H), 7.50 (d, J=5.4 Hz, 2H), 7.56 (d, J=5.4 Hz, 2H), 7.87 (br, 1H), 8.06 (br, 1H), 8.89 (br, 2H).

The Synthesis of Sn-DTBC Compound

The DTBC (315.6 g, 0.296 mmol) is placed in a 100 mL double-necked flask under vacuum and to be baked therein for three times, 20 mL anhydrous tetrahydrofuran is added thereinto, and then the tert-butyllithium (t-BuLi, 1.6 M, 0.74 mL, 1.184 mmol) is slowly dropped thereinto under −78° C. (by mixing the aetone and the liquid nitrogen) for reacting for 1 hr. The chlorotrimethylstannane (1.0 M, 2.4 mL, 2.4 mmol) is added into the mixture under −78° C., and the mixture is returned to the room temperature for reacting 15 hrs. The reaction is terminated by adding water, and the organic solvent is removed under lowered pressure. The organic layer is collected by extracting with ether (50 mL×3) and pure water (50 mL), and the collected organic layer is dried over magnesium sulfate ($MgSO_4$). After removal of the organic solvent under lowered pressure, a yellow sticky Sn-DTBC is obtained (405.7 mg, 98.5%). $^1$H NMR ($CDCl_3$, 300 MHz, ppm): 0.51 (s, 18H), 0.75 (t, J=6.6 Hz, 6H), 0.92 (t, J=6.3 Hz, 12H), 1.05-1.20 (m, 18H), 1.22-1.50 (m, 42H), 1.64-1.77 (m, 8H), 1.82-1.99 (m, 4H), 1.99-2.05 (m, 2H), 2.55-2.61 (m, 2H), 3.15 (t, J=7.8 Hz, 4H), 3.33 (t, J=7.5 Hz, 4H), 4.70-4.80 (m, 1H), 7.61 (s, 2H), 7.92 (br, 1H), 8.10 (br, 1H), 8.89 (br, 2H).

The synthetic processes of the polymer PDTBCDTBT are provided as follows.

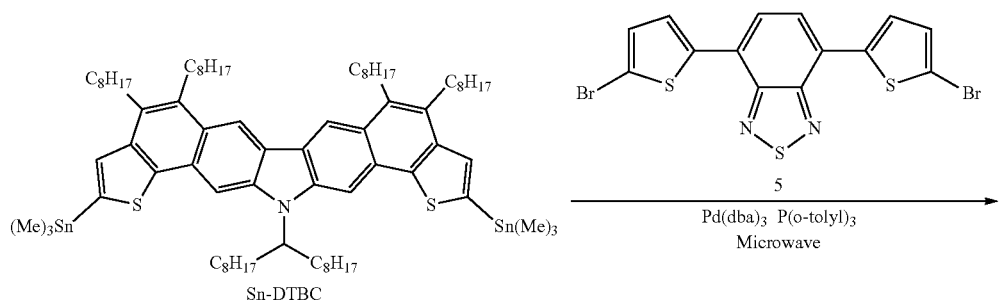

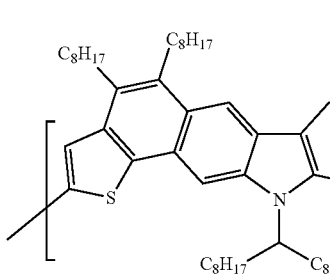

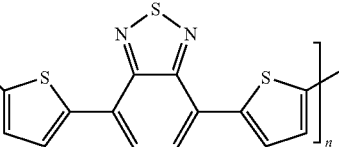

PDTBCDTBT  53%

The Sn-DTBC (306 mg, 0.220 mmol), the compound 5 (100.7 mg, 0.220 mmol), tris(dibenzylideneacetone)dipalladium (10.1 mg, 0.011 mmol) and tri(2-methylphenyl)phosphine (26.8 mg, 0.088 mmol) are placed in a 50 mL single-necked flask, and 7.5 mL of chlorobenzene pre-degassed with nitrogen is added into the flask. The mixture is degassed with nitrogen for 10 min, and the flask is equipped with a reflux condenser and then being moved into a focused microwave synthesizer for microwave polymerization under a condition of 270 watt at 180° C. for 50 min. In turn, the end-capping 2-(tributylstannyl)thiophene (41.0 mg, 0.110 mmol) is added into the mixture for microwave polymerization under 270 watt at 180° C. for 10 min, and 2-bromothiophene (19.7 mg, 0.121 mmol) is added thereinto for reacting under the same condition. Then, 200 mL methanol is used for re-precipitation and the solid is collected by gravity filtration. After the solid is continuously extracting with the acetone for one day, it is continuously extracting with 4:1 hexane/tetrahydrofuran for two days. The solid is resolved in the hot toluene, and 5 eq. of Si-Thiol (47.5 mg, 0.055 mmol) and a magnetic stirrer are added for demetalization for 12 hr. After the Si-Thiol is filtered by gravity, the organic solvent is removed under lowered pressure and the residue is re-recipitated by methanol. After filtration, the PDTBCDTBT as a black green solid is obtained (159 mg, 53%).

The synthetic processes of the polymers PDTSCBT and PDTPCBT are provided as follows.

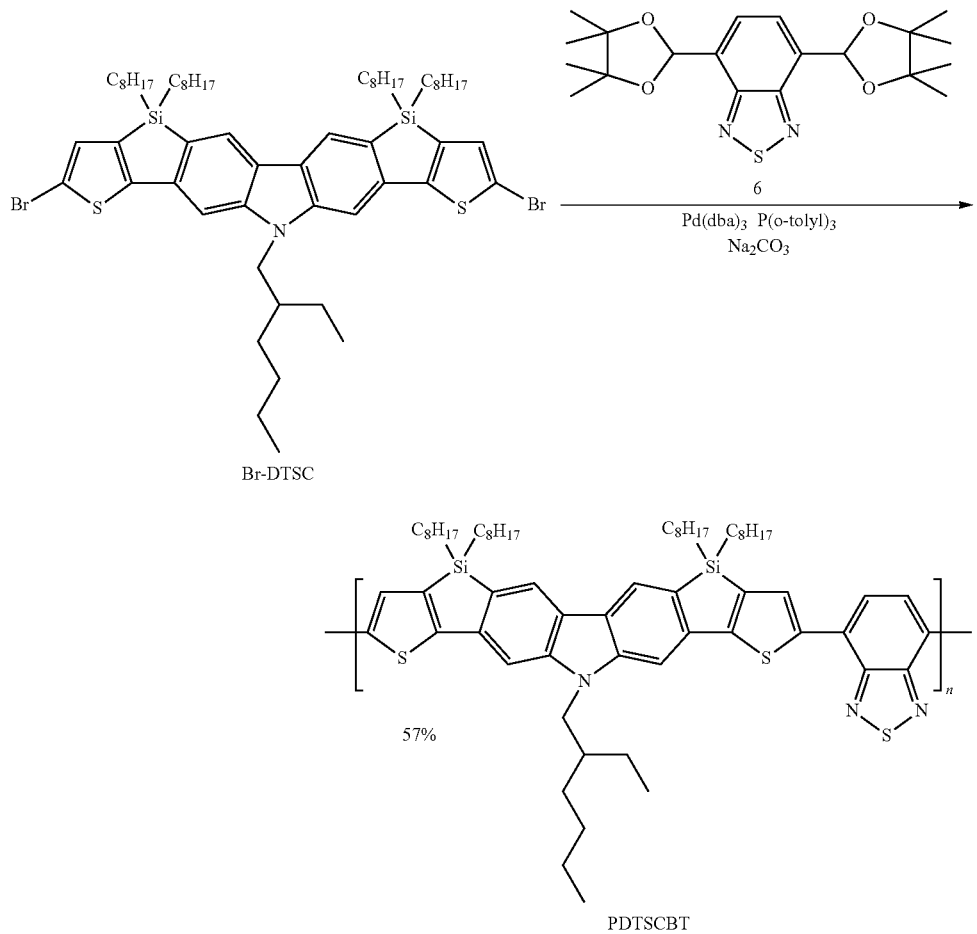

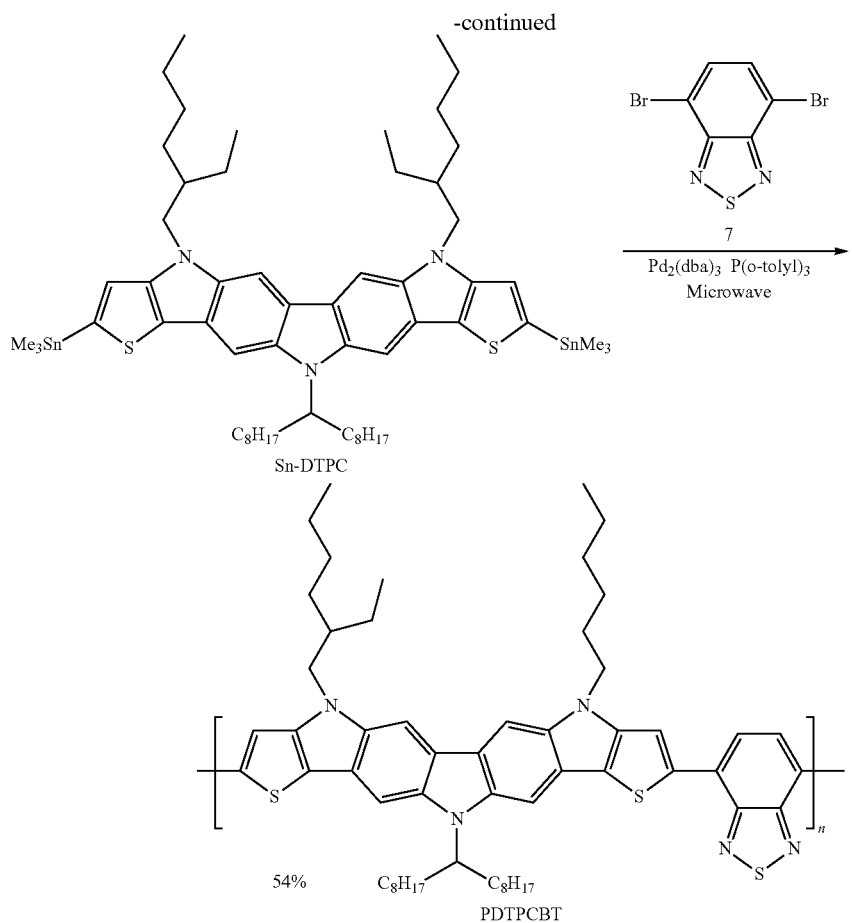

The Br-DTBC (0.43 g, 0.389 mmol), the compound 6 (4,7-bis(4,4,5,5-tetramethyl-1,3,2-dioxaborolan-2-yl)benzo[c][1,2,5]thiadiazole, 0.151 g, 0.389 mmol), tris(dibenzylideneacetone)dipalladium (14.2 mg, 0.016 mmol), tri(2-methylphenyl)phosphine (37.9 mg, 0.125 mmol) and the surfactant (Alivant 336, two drop) are placed in a 100 mL double-necked flask, and 24 mL toluene pre-degassed with nitrogen/1.0M sodium bicarbonate (5:1) are added into the flask. The mixture is degassed with nitrogen for 10 min, and the mixture is heated at 90° C. at reflux under nitrogen. After 30 min, the solution is dropped into 200 mL methanol/pure water (3:1) for reprecipitation and the solid is collected by gravity filtration. The solid is continuously extracting with the acetone for one day, continuously extracting with hexane for one day, and continuously extracting with tetrahydrofuran for two days. The solid is resolved in the hot dichlorobenzene, and 5 eq. of Si-Thiol (69.2 mg, 0.08 mmol) and a magnetic stirrer are added for demetalization for 12 hr. After the Si-Thiol is filtered by gravity, the residue is re-recipitated by methanol. After filtration, the PDTSCBT as a black solid is obtained (240 mg, 57%).

Synthesis of the PDTPCBT Polymer

The Sn-DTPC (400 mg, 0.349 mmol), the compound 7 (4,7-dibromo-2,1,3-benzothiadiazole, 103 mg, 0.349 mmol), tris(dibenzylideneacetone)dipalladium (12.8 mg, 0.014 mmol) and tri(2-methylphenyl)phosphine (34.0 mg, 0.112 mmol) are placed in a 50 mL single-necked flask, and 10 mL chlorobenzene pre-degassed with nitrogen is added into the flask. The mixture is degassed with nitrogen for 10 min, and the flask is equipped with a reflux condenser and then being moved into a focused microwave synthesizer for microwave polymerization under a condition of 270 watt at 180° C. for 50 min. In turn, the end-capping 2-(tributylstannyl)thiophene (65 mg, 0.175 mmol) is added into the mixture for microwave polymerization under 270 watt at 180° C. for 10 min, and 2-bromothiophene (31 mg, 0.188 mmol) is added thereinto for reacting under the same condition. Then, 200 mL methanol is used for re-precipitation and the solid is collected by gravity filtration. After the solid is continuously extracting with the acetone for one day, it is continuously extracting with hexane for one day. The solid is resolved in the tetrahtdrofuran, and 5 eq. of Si-Thiol (60.5 mg, 0.07 mmol) and a magnetic stirrer are added for demetalization for 12 hr. After the Si-Thiol is filtered by gravity, the residue is re-recipitated by methanol. After filtration, the PDTPCBT as a black solid is obtained (180 mg, 54%). Mn=36.4 kDa, PDI=1.21° $^1$H NMR (CDCl3, 300 MHz, ppm): 0.71-1.55 (m, 54H), 2.01 (br, 8H), 2.51 (br, 2H), 4.25 (br, 4H), 4.68 (br, 1H), 7.05 (br, 2H), 7.38-7.51 (br, 4H), 8.31 (br, 2H).

The synthetic processes of the heptacyclic multielectron monomer Br-DTCF are provided as follows.

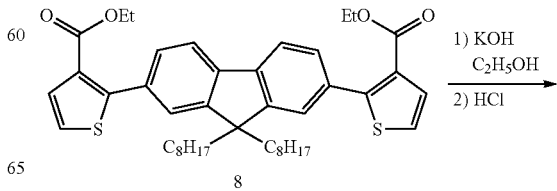

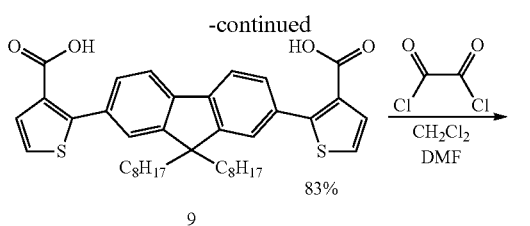

9

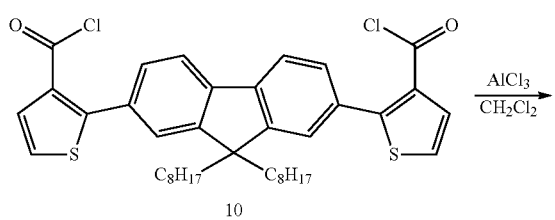

10

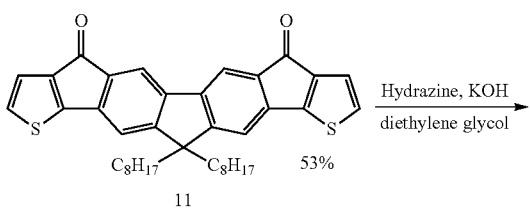

11

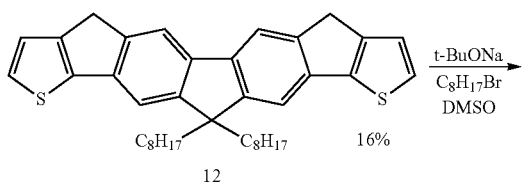

12

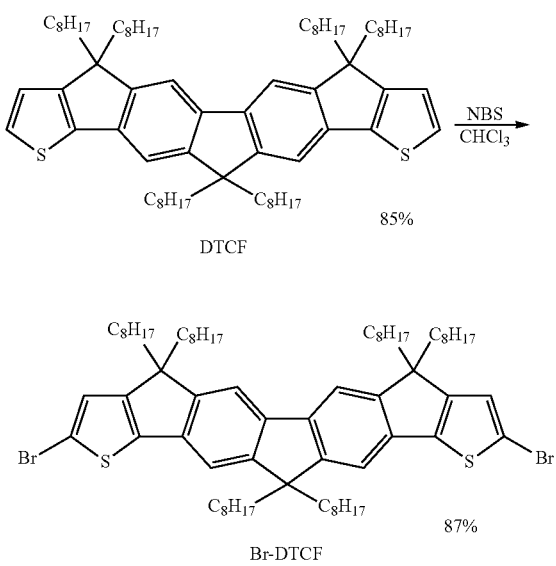

DTCF

Br-DTCF

Synthesis of the Compound 9

The compound 8 (3.62 g, 5.18 mmol) is placed in a 250 mL double-necked flask and the flask is then equipped with the reflux condenser and the sleeve stopper. After dissolving the compound 8 in 150 mL ethanol, the sodium hydroxide (2.90 g, 72.5 mmol) and the distilled water (30 mL) are added into the solution for being heating under 90° C. at reflux for 12 hr. The mixture is cooled to the room temperature, the ethanol is removed by a rotary evaporator, and 1M hydrochloric acid is added to the residue under ice bath until the mixture is acid. After suction filtration, a white solid (2.77 g, 83%) is collected. $^1$H-NMR (300 MHz, CDCl3, δ ppm): 1.85-1.79 (m, 4H), 1.16-0.72 (m, 30H), 7.25 (d, J=5.4 Hz, 2H), 7.36 (s, 1H), 7.41 (d, J=7.8 Hz, 2H), 7.61 (d, J=5.4 Hz, 2H), 7.66 (d, J=7.8 Hz, 2H).

Synthesis of the Compound 11

The compound 9 (4.28 g, 6.66 mmol) is placed in a 250 mL double-necked flask and the flask is then equipped with the one-way valve and the sleeve stopper for being baked under vacuum. 100 mL anhydrous dichloromethane is added into the flask, the oxalyl dichloride (3.38 g, 26.63 mmol) is dropped into the flask and 1 mL N,N-dimethylformide (DMF) (1 v %) is slowly dropped into the flask for incubating 12 hr at room temperature. The liquid is removed under lowered pressure to obtain a yellow solid. This solid is dissolved in 70 mL anhydrous dichloromethane, the additional aluminum chloride (2.34 g, 17.55 mmol) is placed into a 500 mL double-nacked flask for being baked under vacuum, and then 400 mL anhydrous dichloromethane is added thereinto. The above solution is sucked by a syringe under the ice bath at 0° C. and being dropped into a 250 mL double-nacked flask, and the solution changes from pale yellow to orange and then reveals black in 3 hr under room temperature. The reaction is terminated by adding 10 mL cold 1M hydrochloric acid, and the dichloromethane is removed by filtration under lowered pressure. The residue is extracted with ethyl acetate and saline (×3) and additional sodium bicarbonate solution, and dried over MgSO$_4$. The residue is purified by column chromatography on silica gel (using 1:25 (v/v) ethyl acetate/hexane as eluent) to give a red orange solid (2.14 g, 53%). $^1$H-NMR (300 MHz, CDCl3, δ ppm): 1.19-0.66 (m, 30H), 2.02-1.97 (m, 4H), 7.08 (s, 2H), 7.15 (d, J=4.8 Hz, 2H), 7.19 (d, J=4.8 Hz, 2H), 7.75 (s, 2H).

Synthesis of the Compound 12

A mixture of the compound 11 (1.02 g, 1.68 mmol) and potassium hydroxide (1.84 g, 32.86 mmol) is placed in a 100 mL double-necked flask and the flask is then equipped with the reflux condenser and the sleeve stopper. The mixture is dissolved by adding 50 mL diethylene glycol, and hydrazine (1.65 g, 32.86 mmol) is slowly dropped thereinto after the solution is heated to 90° C. The solution is black when it is heated to 180° C. and being incubated for 24 hr. Return to the room temperature, the solution is extracted with ether and saline (×3) and the organic layer is collected and dried over MgSO$_4$. The residue is purified by column chromatography on silica gel (using hexane as eluent) to give a beige solid (0.16 g, 16%). $^1$H-NMR (300 MHz, CDCl3, δ ppm): 1.27-0.67 (m, 30H), 2.07-2.02 (m, 4H), 3.75 (s, 4H), 7.13 (d, J=5.1 Hz, 2H), 7.31 (d, J=5.1 Hz, 2H), 7.42 (s, 2H), 7.77 (s, 2H).

Synthesis of the Compound DTCF

The compound 12 (0.3 g, 0.52 mmol) is placed in a 100 mL double-necked flask and the flask is then equipped with the reflux condenser and the sleeve stopper for being baked under vacuum. 20 mL anhydrous dimethyl sulfoxide (DMSO) is added into the flask under nitrogen. Sodium t-butoxide (0.3 g, 3.12 mmol) dissolved in 15 mL anhydrous DMSO is placed into another 100 mL double-necked flask equipped with a one-way valve and the sleeve stopper, which is sucked by a syringe at 80° C. and slowly dropped into the above-mentioned double-necked flask to make the solution changes from pale yellow to black brown. After incubating for one hour, 1-bromooctane (0.6 g, 3.10 mmol) is slowly dropped into the flask and the flask is heated to 90° C. for 4 hr. After cooling to the room temperature, the reaction is terminated by slowly adding 10 mL distilled water, the mixture is extracted with ether and saline (×3) and dried over MgSO$_4$. After the residue is concentrated under lowered pressure, it is purified by column chromatography on silica gel (using hexane as eluent) to give a yellowish-brown sticky liquid (0.45 g, 85%). $^1$H-NMR (300 MHz, CDCl3, δ ppm): 1.28-0.67 (m, 90H), 2.05-1.86 (m, 12H), 6.99 (d, J=4.8, 2H), 7.27 (d, J=4.8, 2H), 7.31 (s, 2H), 7.57 (s, 2H).

Synthesis of the Compound Br-DTCF

The compound DTCF (0.45 g, 0.44 mmol) is placed into a 50 mL single-necked flask, and 20 mL of CHCl$_3$ is added into the flask for dissolving the compound. After slowly adding the NBS (0.17 g, 0.96 mmol), the mixture is incubated at room temperature for 12 hr. Then, the CHCl$_3$ is removed by concentrated under lowered pressure, and the residue is extracted with ether and saline (×3) and dried over MgSO$_4$. The residue is purified by column chromatography on silica gel (using hexane as eluent) to give a pale yellow solid (0.45 g, 87%). $^1$H-NMR (300 MHz, CDCl3, δ ppm): 1.27-0.64 (m, 90H), 1.99-1.86 (m, 12H), 7.00 (s, 2H), 7.23 (s, 2H), 7.54 (s, 2H).

The synthetic processes of the polymer PDTCFBT are provided as follows.

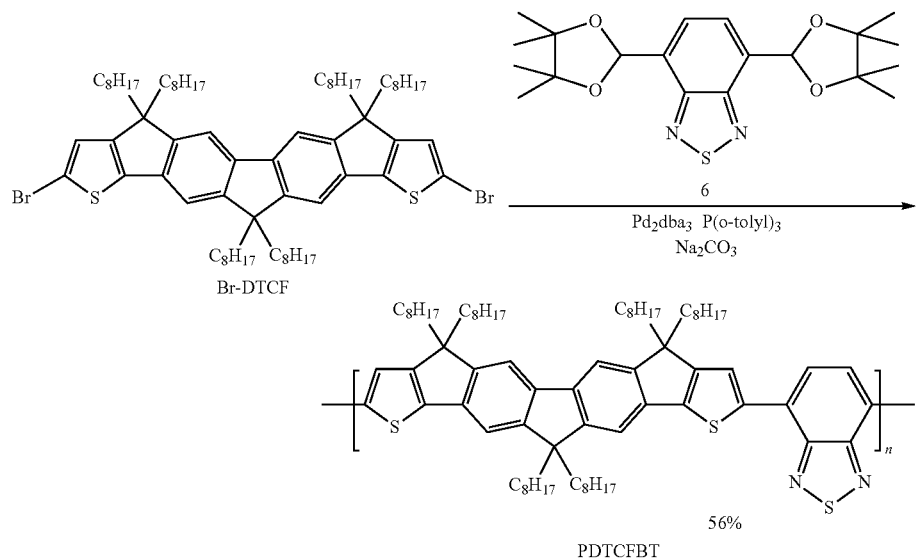

A mixture of Br-DTCF (150 mg, 0.127 mmol), the compound 6 (49.1 mg, 0.127 mmol), Pd$_2$(dba)$_3$ (4.6 mg, 0.005 mmol), P(o-tolyl)$_3$ (12.32 mg, 0.04 mmol) and a drop of Aliquat 336 is placed in a 20 mL seal tube and 1M sodium bicarbonate solution is prepared. 5.4 mL of 1:5 (v/v) toluene/1M sodium bicarbonate solution is added into the solution and degassed by nitrogen for 10 min. After heating the reaction under 90° C. for 72 hr, one drop of bromobenzene is added into the reaction for continuously heating the reaction for 12 hr, and one more drop of 4,4,5,5-tetramethyl-2-phenyl-1,3,2-dioxaborolane is added thereinto for reacting for 12 hr. The above solution is slowly dropped into the methanol, the solid is collected by gravity filtration and washed by the methanol and the distilled water for three times to remove the salt, and the soxhlet extraction is carried out in turn by acetone and hexane. Then, the remaining solid is collected and dissolved in THF and added by Pd-thio gel (Silicycle Inc.) for removing the Pd catalyst for 12 hr. The resulting solution is concentrated under lowered pressure for removing THF and being dropped into the methanol for re-precipitation. The polymer PDTCFBT as a blue black solid is collected by gravity filtration (87 mg, 56%). $^1$H-NMR (300 MHz, CDCl3, δ ppm): 0.70-1.36 (br, 90H), 1.93-2.20 (br, 12H), 7.35 (br, 2H), 7.54-7.57 (br, 2H), 7.85-7.90 (br, 2H), 8.04 (br, 2H). Mn=33054 g/mol, Mw=94733 g/mol, PDI=2.87.

The synthetic processes of the polymers PBBCPDTTPD, PBBCPDTBT and PBBCPDTBT-F are provided as follows.

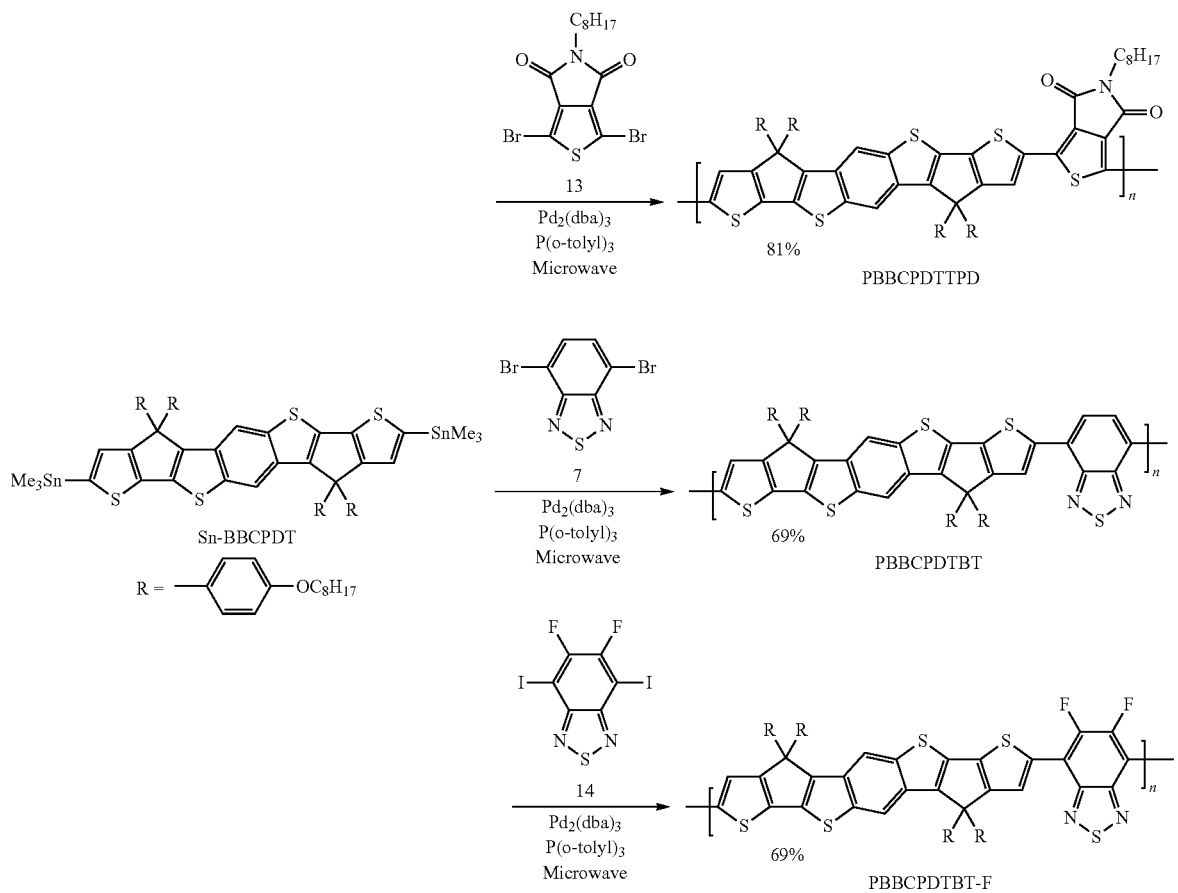

The synthesis of the Polymer PBBCPDTTP

The Sn-BBCPDT (180 mg, 0.118 mmol), the compound 13 (thieno[3,4-c]pyrrole-4,6-dione, 50.0 mg, 0.118 mmol), tris(dibenzylideneacetone)dipalladium (4.3 mg, 0.005 mmol) and tri(2-methylphenyl)phosphine (11.5 mg, 0.04 mmol) are placed in a 50 mL single-necked flask, and 7 mL of chlorobenzene pre-degassed with nitrogen is added into the flask. The mixture is degassed with nitrogen for 10 min, and the flask is equipped with a reflux condenser and then being moved into a focused microwave synthesizer for microwave polymerization under a condition of 270 watt at 180° C. for 50 min. In turn, the end-capping 2-(tributylstannyl)thiophene (22.3 mg, 0.06 mmol) is added into the mixture for microwave polymerization under 270 watt at 180° C. for 10 min, and 2-bromothiophene (9.6 mg, 0.064 mmol) is added thereinto for reacting under the same condition. Then, 200 mL methanol is used for re-precipitation and the solid is collected by gravity filtration. After the solid is continuously extracting with the acetone for one day, it is continuously extracting with hexane for one day. The solid is resolved in the tetrahydrofuran, and 5 eq. of Si-Thiol (21.6 mg, 0.025 mmol) and a magnetic stirrer are added for demetalization for 12 hr. After the Si-Thiol is filtered by gravity, the residue is re-recipitated by methanol. After filtration, the polymer PBBPDTTPD as a dark purplish red solid is obtained (140 mg, 81%). Mn=24.5 kDa, PDI=3.06.

Synthesis of Polymer PBBCPDTBT

The Sn-BBCPDT (200 mg, 0.131 mmol), the compound 7 (2,1,3-benzothiadiazole, 38.6 mg, 0.131 mmol), tris(dibenzylideneacetone)dipalladium (4.8 mg, 0.005 mmol) and tri(2-methylphenyl)phosphine (12.7 mg, 0.05 mmol) are placed in a 50 mL single-necked flask, and 8 mL of chlorobenzene pre-degassed with nitrogen is added into the flask. The mixture is degassed with nitrogen for 10 min, and the flask is equipped with a reflux condensor and then being moved into a focused microwave synthesizer for microwave polymerization under a condition of 270 watt at 180° C. for 50 min. In turn, the end-capping 2-(tributylstannyl)thiophene (24.7 mg, 0.065 mmol) is added into the mixture for microwave polymerization under 270 watt at 180° C. for 10 min, and 2-bromothiophene (11.5 mg, 0.07 mmol) is added thereinto for reacting under the same condition. Then, 200 mL methanol is used for re-precipitation and the solid is collected by gravity filtration. After the solid is continuously extracting with the acetone for one day, it is continuously extracting with hexane for one day. The solid is resolved in the tetrahydrofuran, and 4 eq. of Si-Thiol (18 mg, 0.021 mmol) and a magnetic stirrer are added for demetalization for 12 hr. After the Si-Thiol is filtered by gravity, the residue is re-recipitated by methanol. After filtration, the polymer PBBCPDTBT as a blackish green solid is obtained (134 mg, 69%). Mn=9.3 kDa, PDI=1.78.

Synthesis of the Polymer PBBCPDTBT-F

The Sn-BBCPDT (163 mg, 0.107 mmol), the compound 14 (5,6-difluoro2,1,3-benzothiadiazole, 45.4 mg, 0.107 mmol), tris(dibenzylideneacetone)dipalladium (3.9 mg, 0.004 mmol) and tri(2-methylphenyl)phosphine (10.4 mg, 0.03 mmol) are placed in a 50 mL single-necked flask, and 6 mL of chlorobenzene pre-degassed with nitrogen is added into the flask. The mixture is degassed with nitrogen for 10 min, and the flask is equipped with a reflux condensor and then being moved into a focused microwave synthesizer for microwave polymerization under a condition of 270 watt at 180° C. for 50 min. In turn, the end-capping 2-(tributylstannyl)thiophene (20.2 mg, 0.058 mmol) is added into the mixture for microwave polymerization under 270 watt at 180° C. for 10 min, and 2-bromothiophene (9.4 mg, 0.076 mmol) is added thereinto for reacting under the same condition. Then, 200 mL methanol is used for re-precipitation and the solid is collected by gravity filtration. After the solid is continuously extracting with the acetone for one day, it is continuously extracting with hexane for one day. The solid is resolved in the tetrahydrofuran, and 4 eq. of Si-Thiol (18 mg, 0.021 mmol) and a magnetic stirrer are added for demetalization for 12 hr. After the Si-Thiol is filtered by gravity, the residue is re-recipitated by methanol. After filtration, the polymer PBBCP-DTBT-F as a blackish green solid is obtained (120 mg, 69%). Mn=49.9 kDa, PDI=1.48.

The synthetic processes of the heptacyclic multielectron monomer Sn-IDTT are provided as follows.

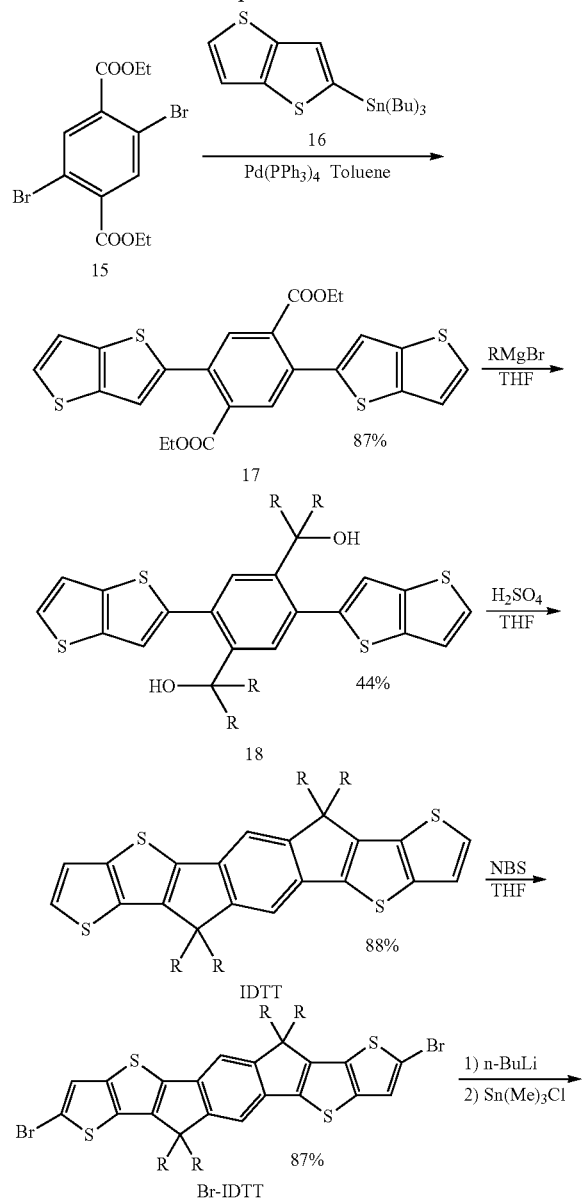

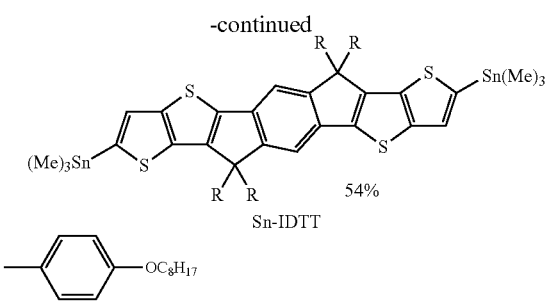

Synthesis of the Compound 17

The compound 15 (diethyl 2,5-Dibromoterephthate, 6.05 g, 15.9 mmol) and the compound 16 (2-(tributylstannyl)thieno[3,2-b]thiophene, 15.71 g, 36.6 mmol) are placed in a 250 mL double-necked flask, and the Pd(PPh$_3$)$_4$ (0.74 g, 0.64 mmol) is added into the double-necked flask in a glove box. After transferring the double-necked flask outside the glove box, 78 mL of toluene pre-degassed by nitrogen is added into the flask. Under the nitrogen, the mixture is heated under 130° C. at reflux for 16 hrs, the organic layer is collected by extracting with ether (100 mL×3) and pure water (150 mL), the collected organic layer is dried over MgSO$_4$, and the organic solvent is removed under lowered pressure. Finally, the residue is purified by column chromatography on silica gel (ethyl acetate/hexane v/v=1/20 as eluent) to give a golden solid 17 (6.9 g, 87%). $^1$H NMR (CDCl3, 300 MHz, ppm): (t, J=6.9 Hz, 6H), 4.21-4.28 (q, J=7.2 Hz, 4H), 7.28 (m, 4H), 7.40 (d, J=5.1 Hz, 2H), 7.88 (s, 2H).

Synthesis of the Compound 18

1.0 M Grignard reagent preparation: The magnesium powder (3.2 g, 132.0 mmol) is placed in a 250 mL double-necked flask to be baked under vacuum for three times, 120 mL anhydrous tetrahydrofuran, 1-bromo-4-(octyloxy)benzene (34.23 g, 120 mmol) and a drop of 1,2-dibromoethane are added thereinto, and the mixture is incubated for 1 hr after being slightly heated. The compound 17 (4.8 g, 9.6 mmol) is placed in a 250 mL double-necked flask to be baked under vacuum for three times, 50 mL anhydrous tetrahydrofuran is added thereinto under nitrogen, and 76.8 mL of freshly prepared Grignard reagent is added into this flask for being heated under 80° C. at reflux for 16 hrs. The mixture is extracted with 150 mL of ammonium chloride, 150 mL of ether (×2) and 100 mL of pure water, and the organic layer is collected and dried over MgSO$_4$. The organic solvent is removed by lowered pressure, and the residue is purified by column chromatography on silica gel (ethyl acetate/hexane v/v=1/10 as eluent) to give a pale yellow solid 18 (5.17 g, 44%). $^1$H NMR (CDCl3, 300 MHz, ppm): 0.86-0.90, (t, J=7.2 Hz, 6H), 1.28-1.45 (m, 20H), 1.75-1.80 (m, 4H), 3.42 (s, 2H), 3.94 (t, J=6.6 Hz, 4H), 6.27 (s, 2H), 6.80 (d, J=9 Hz, 4H), 6.89 (s, 2H), 7.08 (d, J=9 Hz, 4H), 7.13 (d, J=5.1 Hz, 2H), 7.29 (d, J=5.1 Hz, 2H).

Synthesis of the Compound IDTT

The compound 18 (1 g, 0.8 mmol) is placed in a 250 mL single-necked flask, 100 mL of tetrahydrofuran and sulfuric acid (1 mL, 19 mmol) are added thereinto for heating to 80° C. and incubating for 1 hr. The mixture is extracted with 100 mL of ether (×3) and 150 mL of pure water (×5), and the organic layer is collected and dried over MgSO$_4$. The organic solvent is removed by lowered pressure, and the residue is purified by column chromatography on silica gel (ethyl acetate/hexane v/v=1/80 as eluent) to give a yellow solid IDTT (0.85 g, 88%). $^1$H NMR (CDCl3, 300 MHz, ppm): (t, J=6.9 Hz, 6H), 1.27-1.45 (m, 20H), 1.71-1.76 (m, 4H), (t, J=6.6 Hz, 4H), 6.79 (d, J=8.7 Hz, 4H), 7.16 (d, J=8.7 Hz, 4H), 7.24-7.28 (d, J=5.1 Hz, 2H), 7.46 (s, 2H).

Synthesis of the Compound Br-IDTT

The IDTT (1.1 g, 0.92 mmol) is placed in a single-necked flask and dissolved by adding 30 mL of tetrahydrofuran into the flask, N-bromosuccimide (0.38 g, 2.12 mmol) is further added into the flask, and the flask is wrapped with an aluminum foil to avoid the light. The reaction is incubated at room temperature under nitrogen for 12 hrs and being terminated by adding water. The organic solvent is removed by lowered pressure, the residue is extracted with 50 mL of ether (×3) and 50 mL of pure water, and the organic layer is collected and dried over $MgSO_4$. The organic solvent is removed by lowered pressure, and the residue is purified by column chromatography on silica gel (hexane as eluent) to give a yellow solid Br-IDTT (1.08 g, 87%). $^1$H NMR (CD2Cl2, 300 MHz, ppm): (t, J=6.9 Hz, 6H), 1.26-1.40 (m, 20H), 1.67-1.76 (m, 4H), (t, J=6.6 Hz, 4H), 6.78 (d, J=8.7 Hz, 4H), 7.12 (d, J=8.7 Hz, 4H), 7.31 (s, 2H), 7.24 (s, 2H), 7.47 (s, 2H).

Synthesis of the Compound Sn-IDTT

The Br-IDTT (0.85 g, 0.63 mmol) is placed in a 100 mL double-necked flask to be baked under vacuum for three times, 30 mL of anhydrous tetrahydrofuran is added thereinto, and the t-BuLi (2.5 M, 0.63 mL, 1.56 mmol) is slowly dropped thereinto under −78° C. (by mixing the acetone and the liquid nitrogen) for reacting for 30 min. The mixture is incubated at room temperature for 30 min and chlorotrimethylstannane (1.0 M, 1.9 mL, 1.89 mmol) is added into the mixture under −78° C., and the mixture is returned to the room temperature for reacting 12 hrs. The reaction is terminated by adding water, and the organic solvent is removed under lowered pressure. The organic layer is collected by extracting with ether (50 mL×3) and pure water (50 mL), and the collected organic layer is dried over $MgSO_4$. After removal of the organic solvent under lowered pressure, hexane is used for re-crystalization and a pale yellow solid Sn-IDTT is obtained (0.52 g, 54%). $^1$H NMR (CDCl3, 300 MHz, ppm): (s, 18H), (t, J=6.9 Hz, 6H), 1.27-1.43 (m, 20H), 1.71-1.76 (m, 4H), (t, J=6.6 Hz, 4H), 6.79 (d, J=9 Hz, 4H), 7.19 (d, J=9 Hz, 4H), 7.30 (s, 2H), 7.42 (s, 2H).

The synthetic processes of the polymers PIDTTBT and PIDTTDTBT are provided as follows.

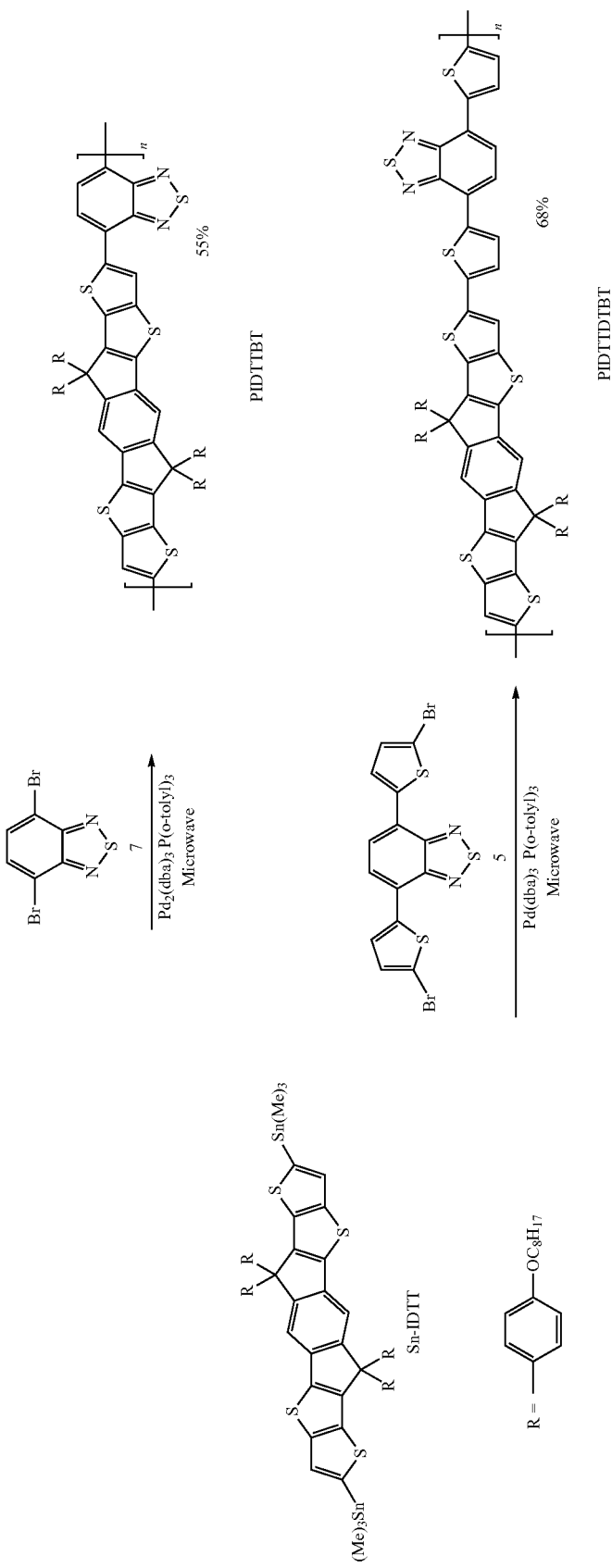

Synthesis of the Polymer PIDTTBT

The Sn-IDTT (160 mg, 0.11 mmol), the compound 7 (32.34 mg, 0.11 mmol), tris(dibenzylideneacetone)dipalladium (4.1 mg, 0.0044 mmol) and tri(2-methylphenyl)phosphine (10.72 mg, 0.035 mmol) are placed in a 50 mL single-necked flask, and 7 mL of chlorobenzene pre-degassed with nitrogen is added into the flask. The mixture is degassed with nitrogen for 10 min, and then the flask is equipped with a reflux condensor and being moved into a focused microwave synthesizer for microwave polymerization under a condition of 270 watt at 180° C. for 50 min. In turn, the end-capping 2-(tributylstannyl)thiophene (20.5 mg, 0.055 mmol) is added into the mixture for microwave polymerization under 270 watt at 180° C. for 10 min, and 2-bromothiophene (9.78 mg, 0.06 mmol) is added thereinto for reacting under the same condition. Then, 200 mL of methanol is used for re-precipitation and the solid is collected by gravity filtration. After the solid is continuously extracting with the acetone for one day, it is continuously extracting with hexane for one day and resolved in the tetrahydrofuran. 5 eq. of Si-Thiol (19.01 mg, 0.022 mmol) and a magnetic stirrer are added for demetalization for 12 hr. After the Si-Thiol is filtered by gravity, the residue is re-recipitated by methanol. After filtration, the polymer PIDTTBT as a dark blue solid is obtained (80 mg, 55%). Mn=19.0 kDa, PDI=1.47.

Synthesis of the Polymer PIDTTDTBT

The Sn-IDTT (100 mg, 0.066 mmol), the compound 5 (30.24 mg, 0.066 mmol), tris(dibenzylideneacetone)dipalladium (2.42 mg, 0.0026 mmol) and tri(2-methylphenyl)phosphine (6.43 mg, 0.021 mmol) are placed in a 50 mL single-necked flask, and 7 mL of chlorobenzene pre-degassed with nitrogen is added into the flask. The mixture is degassed with nitrogen for 10 min, and the flask is equipped with a reflux condensor and then being moved into a focused microwave synthesizer for microwave polymerization under a condition of 270 watt at 180° C. for 50 min. In turn, the end-capping 2-(tributylstannyl)thiophene (12.31 mg, 0.033 mmol) is added into the mixture for microwave polymerization under 270 watt at 180° C. for 10 min, and 2-bromothiophene (5.87 mg, 0.036 mmol) is added thereinto for reacting under the same condition. Then, 200 mL methanol is used for re-precipitation and the solid is collected by gravity filtration. After the solid is continuously extracted with the acetone for one day, it is continuously extracted with hexane for one day. The solid is resolved in the tetrahydrofuran, and 5 eq. of Si-Thiol (19.01 mg, 0.022 mmol) and a magnetic stirrer are added for demetalization for 12 hr. After the Si-Thiol is filtered by gravity, the residue is re-recipitated by methanol. After filtration, the polymer PIDTTDTBT as a dark black red solid is obtained (60 mg, 68%). Mn=26.5 kDa, PDI=2.6.

The synthetic processes of the hexacyclic multielectron monomer B-DITT are provided as follows.

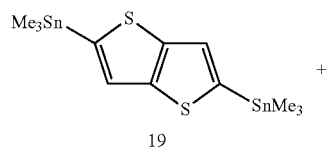

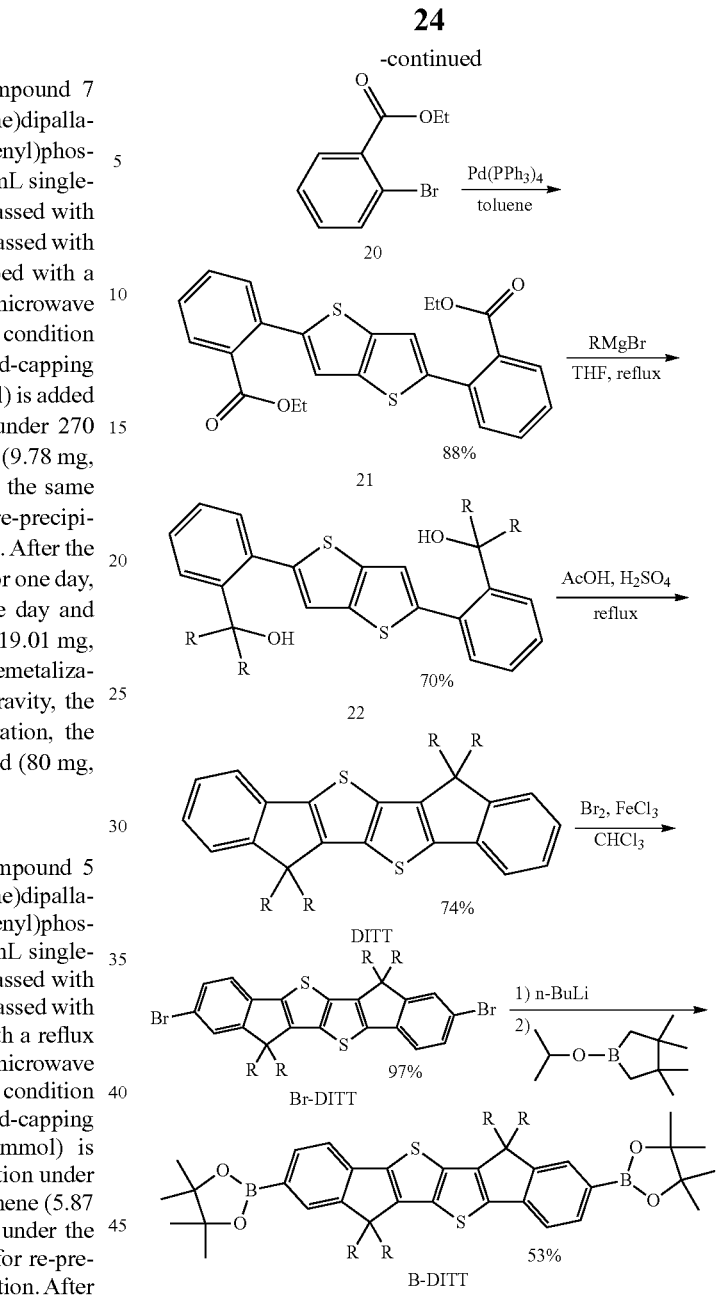

The synthesis of the Compound 21

The compound 19 (5,5'-Bis(trimethylstannyl)thieno[2,3-d]dithiophene, 2 g, 4.3 mmol) and the compound 20 (ethyl 2-bromobenzoate are placed in a 100 mL double-necked flask, and the Pd(PPh$_3$)$_4$ (250 mg, 0.2 mmol) is added into the double-necked flask in a glove box. After transferring the double-necked flask outside the glove box, 43 mL of toluene pre-degassed by nitrogen is added into the flask. Under the nitrogen, the mixture is heated under 130° C. at reflux for 16 hrs, the organic layer is removed by a rotary evaporator under lowered pressure. Then, the residue is purified by column chromatography on silica gel (ethyl acetate/hexane v/v=20/1 as eluent) to quickly give a yellow solid, and this solid is re-crystalized with the ethanol to give a yellow powder 21 (1.65 g, 88%). $^1$H NMR (CDCl3, 300 MHz, ppm): (t, J=6.9 Hz, 6H), 4.29-4.36 (q, J=7.2 Hz, 4H), 7.30 (d, J=5.4 Hz, 2H), 7.55 (d, J=5.4 Hz, 2H), 7.52 (s, 2H), 8.21 (s, 2H).

Synthesis of the Compound 22

1.5 M Grignard reagent preparation: The magnesium powder (2.23 g, 97.73 mmol) is placed in a 250 mL double-necked flask to be baked under vacuum for three times, 90 mL of anhydrous tetrahydrofuran, 1-bromo-4-(octyloxy)benzene (26.10 g, 91.51 mmol) and three drops of 1,2-dibromoethane are added thereinto, and the mixture is incubated for 1 hr after being slightly heated. The compound 21 (4.00 g, 9.16 mmol) is placed in a 500 mL double-necked flask to be baked under vacuum for three times, 100 mL of anhydrous tetrahydrofuran is added thereinto under nitrogen, and 92 mL of freshly prepared Grignard reagent is added into this flask for being heated under 80° C. at reflux for 16 hrs. The mixture is extracted with 150 mL of ammonium chloride, 150 mL of ether (×2) and 100 mL of pure water, and the organic layer is collected and dried over MgSO$_4$. The organic solvent is removed by lowered pressure, and the residue is purified by column chromatography on silica gel (dichloromethane/hexane v/v=1/10 as eluent) to give a yellow sticky 22 (7.5 g, 70%). $^1$H NMR (CDCl3, 300 MHz): 0.88 (t, J=6.5 Hz, 12H), 1.20-1.50 (m, 40H), 1.78 (m, 8H), 3.42 (s, 2H), 3.95 (t, J=6.5 Hz, 8H), 6.26 (s, 2H), 6.81 (d, J=9.0 Hz, 8H), 7.05 (d, J=9.0 Hz, 8H), 7.19-7.35 (m, 8H).

Synthesis of the Compound DITT

The compound 22 (3.00 g, 2.56 mmol) is placed in a 250 mL single-necked flask, 72 mL of acetic acid and a drop of sulfuric acid are added thereinto for heating to 80° C. and incubating for 1 hr. The mixture is extracted with 100 mL of sodium bicarbonate (×2) and 50 mL of ethyl acetate (×2), and the organic layer is collected and dried over MgSO$_4$. The organic solvent is removed by lowered pressure, and the residue is purified by column chromatography on silica gel (dichloromethane/hexane v/v=1/20 as eluent) to give a yellowish brown solid DITT (2.16 g, 74%). $^1$H NMR (CDCl3, 300 MHz): 0.87 (t, J=6.6 Hz, 12H), 1.20-1.55 (m, 40H), 3.88 (t, J=6.5 Hz, 8H), 6.78 (d, J=8.9 Hz, 8H), 7.16 (d, J=8.9 Hz, 8H), 7.20-7.30 (m, 4H), 7.35 (d, J=7.8 Hz, 2H), 7.38 (d, J=7.8 Hz, 2H).

Synthesis of the Compound Br-DITT

The DITT (0.50 g, 0.44 mmol) is placed in a 50 mL double-necked flask, 15.4 mL of chloroform is poured thereinto, and 9.3 mg of ferric trichloride is added into the flask under room temperature for reacting for 12 hrs. The reaction is terminated by adding water, the organic solvent is removed by lowered pressure, the residue is extracted with 50 mL of ether (×3) and 50 mL of pure water, and the organic layer is collected and dried over MgSO$_4$. The organic solvent is removed by lowered pressure, and the hexane is used for recrystallization to give a pale yellow solid Br-DITT (0.55 g, 97%). $^1$H NMR (CDCl3, 300 MHz): 0.87 (t, J=6.3 Hz, 12H), 1.20-1.50 (m, 40H), 1.74 (m, 8H), 3.89 (t, J=6.5 Hz, 8H), 6.80 (d, J=9.0 Hz, 8H), 7.12 (d, J=9.0 Hz, 8H), 7.20 (d, J=8.1 Hz, 2H), 7.39 (d, J=8.1 Hz, 2H), 7.48 (s, 2H).

Synthesis of the Compound B-DITT

The Br-DITT (1.00 g, 0.77 mmol) is placed in a 100 mL double-necked flask to be baked under vacuum for three times, 27 mL of anhydrous tetrahydrofuran is added thereinto, and the t-BuLi (2.5 M, 1 mL, 2.44 mmol) is slowly dropped thereinto under −78° C. (by mixing the acetone and the liquid nitrogen) for reacting for 1 hr. The mixture is incubated at room temperature for 20 min and the boron ester reagent (2-isopropoxy-4,4,5,5-tetramethyl-1,3,2-dioxaborolane, 0.58 M, 3.12 mmol) is added into the mixture under −78° C., and the mixture is returned to the room temperature for reacting 12 hrs. The reaction is terminated by adding water, and the organic solvent is removed under lowered pressure. The organic layer is collected by extracting with ether (150 mL×3) and pure water (50 mL), and the collected organic layer is dried over MgSO$_4$. After removal of the organic solvent under lowered pressure, hexane is used for re-crystalization and a pale yellow solid B-DITT is obtained (0.57 g, 53%). $^1$H NMR (CDCl3, 300 MHz): 0.86 (t, J=5.9 Hz, 12H), 1.20-1.1.40 (m, 40H), 1.72 (m, 64H), 3.88 (t, J=6.5 Hz, 8H), 6.77 (d, J=8.6 Hz, 8H), 7.16 (d, J=8.6 Hz, 8H), 7.34 (d, J=7.5 Hz, 2H), 7.73 (d, J=7.5 Hz, 2H), 7.78 (s, 2H).

The synthetic processes of the polymers PDITTBT and PDITTDTBT are provided as follows.

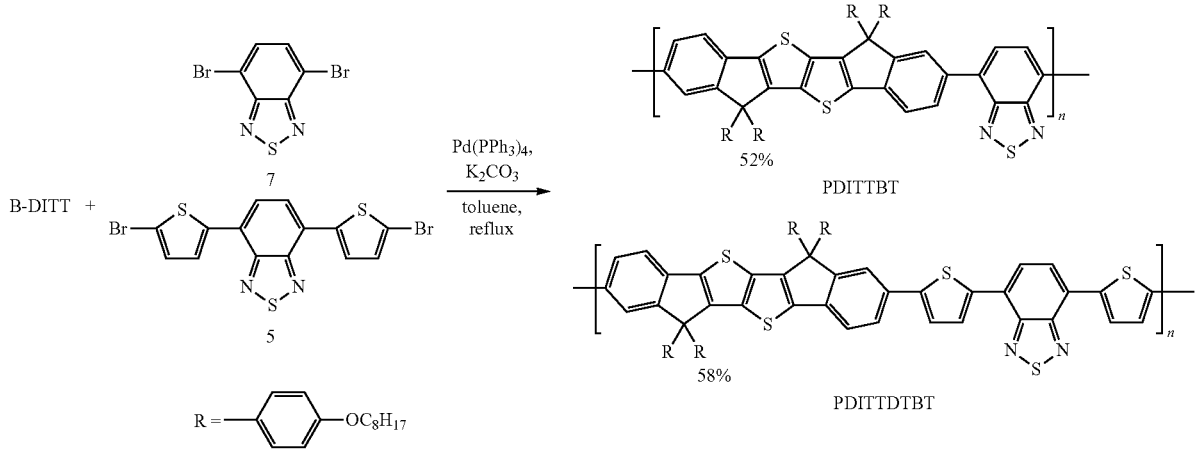

Synthesis of the Polymer PDITTBT

The B-DITT (216.8 mg, 0.16 mmol), the compound 7 (46 mg, 0.16 mmol), Pd(PPh$_3$)$_4$ (3.6 mg, 0.0031 mmol), K$_2$CO$_3$ (163.3 mg, 1.18 mmol) and Aliquat 336 (27 mg, 0.07 mmol) are placed in a 25 mL single-necked flask, and 5 mL of toluene pre-degassed with nitrogen and 1 mL of distilled water are poured into the flask. The mixture is degassed with nitrogen for 10 min, and then the flask is equipped with a reflux condensor for polymerization at 90° C. for 72 hrs. Then, 400 mL of methanol is used for re-precipitation and the solid is collected by gravity filtration. After the solid is continuously extracting with the acetone for one day, it is continuously extracting with hexane for one day and resolved in the tetrahydrofuran. 4 eq. of Si-Thiol (10.8 mg, 0.64 mmol) and a magnetic stirrer are added for demetalization for 12 hr.

After the Si-Thiol is filtered by gravity, the residue is re-precipitated by methanol. After filtration, the polymer PDITTBT as a black green solid is obtained (103 mg, 52%). Mn=19.0 kDa, PDI=1.76.

Synthesis of the Polymer PDITTDTBTBT

The B-DITT (216.8 mg, 0.16 mmol), the compound 5 (71.5 mg, 0.16 mmol), Pd(PPh₃)₄ (3.6 mg, 0.0031 mmol), K₂CO₃ (163.3 mg, 1.18 mmol) and Aliquat 336 (27 mg, 0.07 mmol) are placed in a 25 mL single-necked flask, and 5 mL of toluene pre-degassed with nitrogen and 1 mL of distilled water are poured into the flask. The mixture is degassed with nitrogen for 10 min, and then the flask is equipped with a reflux condensor for polymerization at 90° C. for 72 hrs. Then, 400 mL of methanol is used for re-precipitation and the solid is collected by gravity filtration. After the solid is continuously extracting with the acetone for one day, it is continuously extracting with hexane for one day and resolved in the tetrahydrofuran. 4 eq. of Si-Thiol (10.8 mg, 0.64 mmol) and a magnetic stirrer are added for demetalization for 12 hr. After the Si-Thiol is filtered by gravity, the residue is re-recipitated by methanol. After filtration, the polymer PDITTDTBTBT as a black green solid is obtained (130 mg, 58%). Mn=8.1 kDa, PDI=2.1.

The synthetic processes of the nonacyclic multielectron monomer Sn-TPTPT are provided as follows.

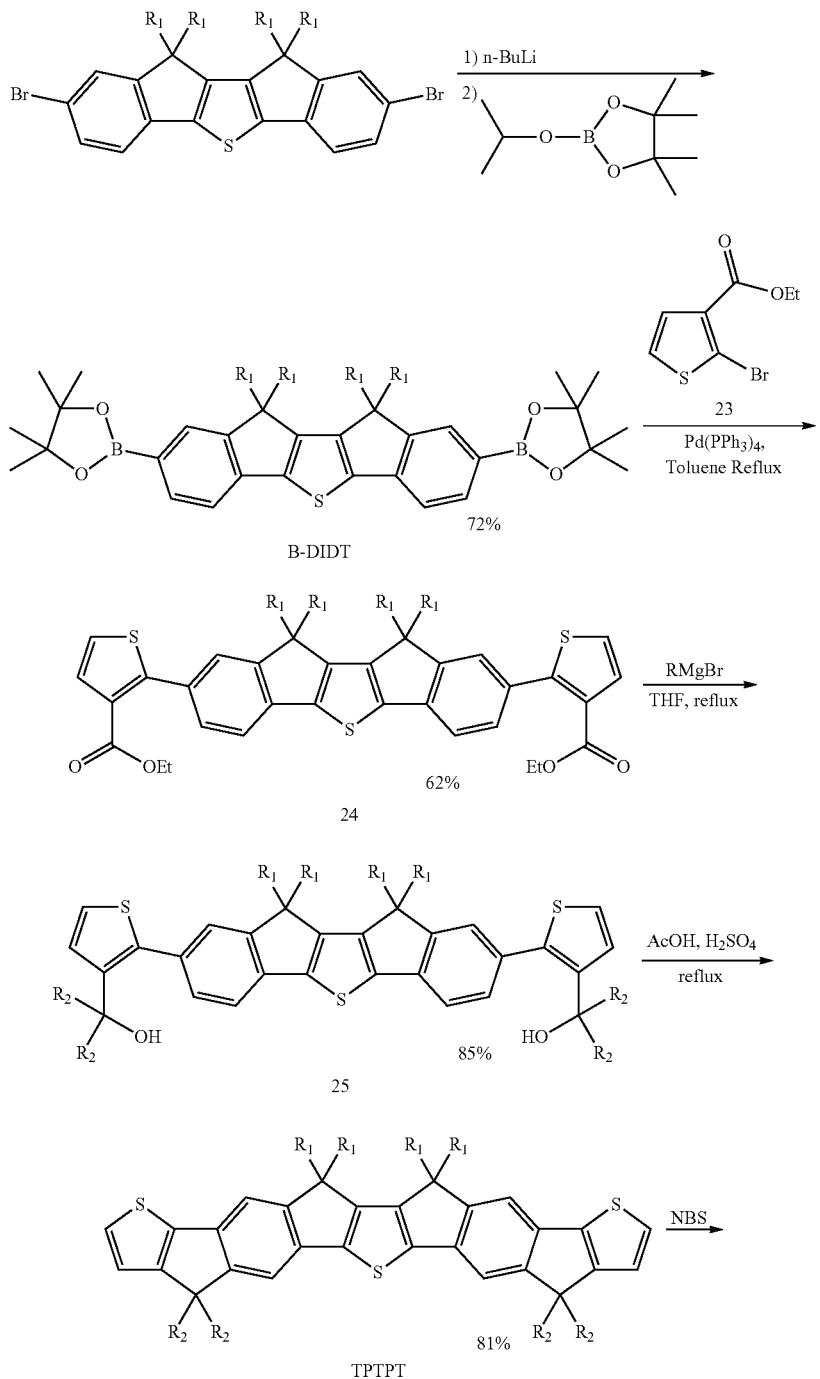

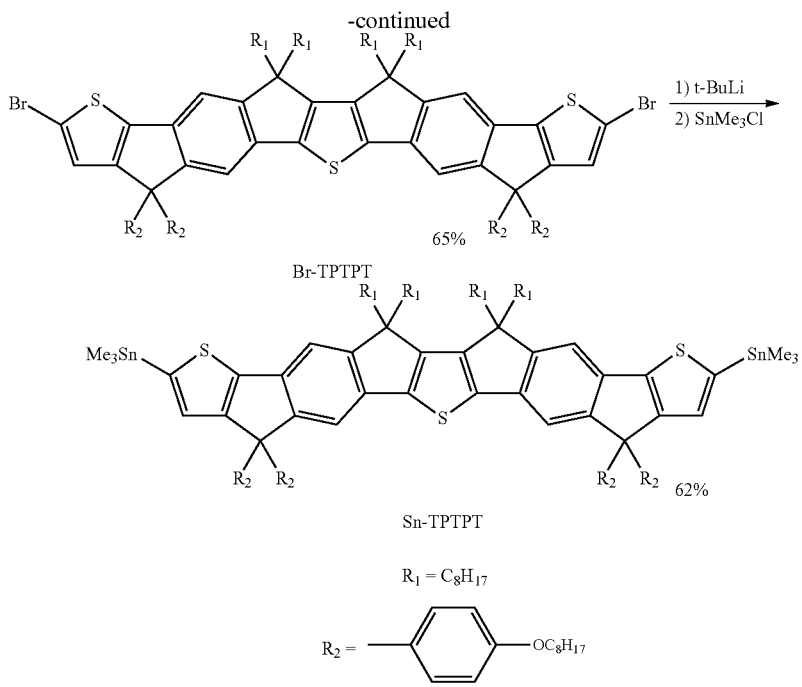

Br-TPTPT

Sn-TPTPT $R_1 = C_8H_{17}$ $R_2 = $ —⌬— $OC_8H_{17}$

Synthesis of the Compound B-DIDT

The Br-DITT (1.06 g, 1.22 mmol) dissolved in 28 mL of anhydrous tetrahydrofuran is placed in a 100 mL double-necked flask and 2.8 M t-BuLi (1.6 mL in hexane, 3.91 mmol) is slowly dropped thereinto under −78° C. After stirring the mixture under −78° C. for 2 hrs, 2-isopropoxy-4,4,5,5-tetramethyl-1,3,2-dioxaborolane (0.91 g, 4.89 mmol) is slowly dropped into the reacting flask and the mixing solution is returned to the room temperature and stirred for 16 hrs continuously. The mixture is extracted with ethyl acetate (300 mL×3) and pure water (150 mL), and the water in the organic layer is removed by the anhydrous $MgSO_4$. The residue is concentrated by rotation, purified by column chromatography on silica gel (hexane/ethyl acetate v/v=40/1 as eluent), and re-crystalized by the methanol to give a yellow solid B-DIDT (0.85 g, 72%). $^1$H NMR (CDCl3, 300 MHz): 7.74 (d, J=7.4 Hz, 2H), 7.60 (s, 2H), 7.37 (d, J=7.4 Hz, 2H), 1.98-2.18 (m, 8H), 1.39 (s, 12H), 0.50-1.30 (m, 60H).

Synthesis of the Compound 24

B-DIDT (2.20 g, 2.29 mmol), ethyl 2-bromothiophene-3-carboxylate (1.24 g, 5.27 mmol), Pd(PPh3)4 (0.265 g, 0.23 mmol), K2CO3 (1.90 g, 13.75 mmol), and Aliquant 336 (0.23 g, 0.57 mmol) in a solution of degassed toluene (17 mL) and degassed $H_2O$ (3.5 mL) are introduced to a 50 mL round-bottom flask. The reaction solution is heated to 90° C. and continuously stirred for 72 hrs. The reaction solution is extracted with ethyl acetate (300 mL×3) and water (150 mL). The combined organic layer was dried over MgSO4. The residue is purified by column chromatography on silica gel (hexane/ethyl acetate, v/v, 20/1) and then recrystallized from hexane to give a light yellow solid 24 (2.07 g, 62%). $^1$H NMR (CDCl3, 300 MHz): δ 7.52 (d, J=5.6 Hz, 2H), 7.51-7.30 (m, 6H), 3.17-3.58 (m, 4H), 7.23 (d, J=5.6 Hz, 2H), 4.20 (q, J=7.2 Hz, 4H), 2.09 (t, J=8.1 Hz, 8H), 1.40-0.96 (m, 54H), 0.82 (t, J=13.4 Hz, 12H).

Synthesis of the Compound 25

A Grignard reagent is prepared by the following procedure. The magnesium turnings (0.8 g, 33.3 mmol) is placed in a 50 mL double-necked flask to be baked under vacuum for three times, 20 mL of anhydrous tetrahydrofuran and 3-4 drops of 1,2-dibromoethane are added thereinto, and 1-bromo-4-(octyloxy)benzene (8.56 g, 30.0 mmol) is slowly added thereinto for evenly stirring 1 h. The compound 24 (0.80 g, 0.79 mmol) is placed in a 100 mL double-necked flask, 20 mL anhydrous tetrahydrofuran is added thereinto for evenly stirring and mixing, and freshly prepared 4-(octyloxy)benzene 1-magnesium bromide (20 mL, 7.9 mmol) is added thereinto dropwise at room temperature. The resulting mixture is heated under 80° C. at reflux and continuously stirred for 16 hrs. The reaction solution is extracted with ethyl acetate (150 mL×3) and water (100 mL) The combined organic layer is dried over MgSO4. The residue is purified by column chromatography on silica gel (hexane/ethyl acetate, v/v, 100/1) to give a yellow oil 25 (1.17 g, 85%). 1H NMR (CDCl3, 300 MHz): δ 7.24 (d, J=9.0 Hz, 2H), 7.17 (d, J=9.0 Hz, 2H), 7.16 (d, J=9.0 Hz, 8H), 7.09 (d, J=5.1 Hz, 2H), 6.94 (s, 2H), 6.84 (d, J=9.0 Hz, 8H), 6.41 (d, J=5.6 Hz, 2H), 3.97 (t, J=6.5 Hz, 8H), 3.07 (s, 2H), 1.95-1.60 (m, 16H), 1.55-0.40 (m, 112H).

The Synthesis of the Compound TPTPT

The compound 25 (2.00 g, 1.14 mmol) is placed in a 250 mL double-necked flask, 116 mL of acetic acid is added for heating and dissolving the compound 25, and 3.5 mL of conc. sulfuric acid is slowly dropped thereinto. The resulting solution is stirred for 18 h at 95° C. and then is extracted with ethyl acetate (500 mL×3) and water (250 mL) The combined organic layer is dried over MgSO4. The residue is purified by column chromatography on silica gel (hexane/ethyl acetate, v/v, 100/1) to give an orange oil TPTPT (1.58 g, 81%). $^1$H NMR (d8-THF, 300 MHz): δ 7.45 (s, 2H), 7.34 (d, J=4.8 Hz, 2H), 7.33 (s, 2H), 7.12 (d, J=8.7 Hz, 8H), 6.99 (d, J=4.8 Hz, 2H), 6.72 (d, J=8.7 Hz, 8H), 3.87 (t, J=6.0 Hz, 8H), 2.3-2.1 (m, 8H), 1.50-0.95 (m, 96H), 0.90-0.70 (m, 24H).

Synthesis of the Compound Br-TPTPT

TPTPT (1.58 g, 0.92 mmol) in chloroform (87 mL) is placed in a 250 mL double-necked flask, N-bromosuccinimide (0.36 g, 2.23 mmol) is added thereinto at room temperature. The flask is wrapped with the aluminum foil and stirred for 12 h at room temperature and then is quenched by water (100 mL) The mixture solution is extracted with chloroform (450 mL×3) and water (150 mL) The combined organic layer is dried over MgSO4. After removal of the solvent under lowered pressure, the residue is purified by column chromatography on silica gel (hexane/ethyl acetate, v/v, 100/1) and then recrystallized from hexane to give an orange solid Br-TPTPT (1.12 g, 65%). $^1$HNMR (CDCl$_3$, 300 MHz): 7.23 (s, 2H), 7.18 (s, 2H), 7.12 (d, J=8.7 Hz, 8H), 6.99 (s, 2H), 6.78 (d, J=8.7 Hz, 8H), 3.90 (t, J=6.5 Hz, 8H), 2.07 (t, J=8.0 Hz, 8H), 1.80-1.70 (m, 8H), 1.50-0.60 (m, 112H).

TPTPT (1.60 g, 0.93 mmol) is placed in a 50 mL double-necked flask, and 28 mL of anhydrous tetrahydrofuran is added thereinto foe evenly stirring and dissolving the TPTPT. 1.6 M t-BuLi in hexane (1.8 mL, 2.80 mmol) is dropwise added into the flask at −78° C. After stirring at −78° C. for 1 h, 1.0 M solution of chlorotrimethylstannane in THF (3.7 mL, 3.73 mmol) is introduced dropwise by syringe to the solution. The mixture solution is quenched with water and extracted with Chloroform (450 mL×3) and water (150 mL) The combined organic layer is dried over MgSO4. After removal of the solvent by a rotary evaporator, Sn-TPTPT (1.18 g, 62%) is obtained as an orange oil and used without further purification. 1H NMR (CDCl$_3$, 300 MHz): δ 7.29 (s, 2H), 7.27 (s, 2H), 7.21 (d, J=8.7 Hz, 8H), 7.06 (s, 2H), 6.81 (d, J=8.7 Hz, 8H), 3.94 (t, J=6.3 Hz, 8H), 2.20-2.00 (m, 8H), 1.85-1.70 (m, 8H), 1.50-0.60 (m, 112H), 0.40 (s, 18H).

The synthetic processes of the polymer PTPTPTBT are provided as follows.

placed in a round bottom flask. The mixing solution is degassed with nitrogen for 10 min at the room temperature, and the flask is moved into a microwave reactor under a condition of 270 watt for 45 min. Then, the tributyl(thiophen-2-yl)stannane (13.1 mg, 0.035 mmol) is added in to the flask under 270 watt for 10 min. Finally, 2-bromothiophene (6.2 mg, 0.038 mmol) is added in to the flask under 270 watt for 10 min. The mixture is dropwise added into the methanol for re-precipitation, the solid is collected by filtration, and the filtrate is continuously extracted with the acetone, the hexane and the chloroform. The Pd-thiol gel (Silicycle Inc.) and Pd-TAAcOH are added into the chloroform solution for removing the remaining catalyst Pd and the metal Sn. After the gel is removed by filtration the solvent is removed by a rotary evaporator, the polymer is re-dissolved in a small amount of chloroform and re-precipitated by the methanol. The purified polymer is collected by filtration and dried under vacuum to give the PTPTPTBT as a dark green strip solid (215 mg, 62%). Mn=30000, PDI=1.69. $^1$H NMR (CDCl$_3$, 300 MHz): 8.20-8.00 (m, 2H), 7.95-7.80 (m, 2H), 7.50-7.30 (m, 4H), 7.25-7.15 (m, 8H), 6.90-6.70 (m, 8H), 4.00-3.80 (m, 8H), 1.85-1.60 (m, 16H), 1.50-1.00 (m, 88H), 0.90-0.70 (m, 24H).

Through the above embodiments, it is known that the present invention provides the chemical structures of various ladder-type multifused arenes and the synthetic methods thereof, and also provides the p-type low bandgap conjugated copolymers by hybriding the ladder-type multifused arenes and the electron deficient acceptor and the synthetic method thereof. Specifically, the present invention is based on various

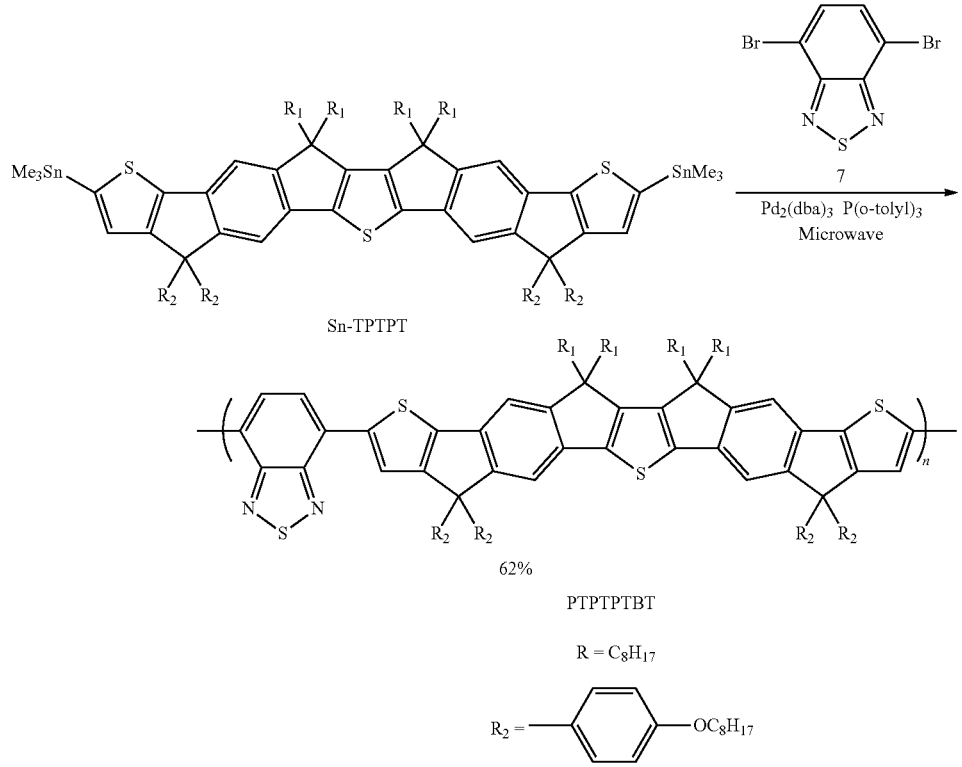

Synthesis of the Polymer PTPTPTBT

Sn-TPTPT (143.0 mg, 0.07 mmol), 7 (20.6 mg, 0.07 mmol) Pd(PPh$_3$)$_4$ (3.2 mg, 0.0035 mmol), tri(o-tolyl)phosphine (6.8 mg, 0.022 mmol) and 3 mL of anhydrous chlorobenzene are ladder-type multifused arenes. By various cyclizations, one or more aromatic ring and/or one or more heterring such as thiophene, pyrrole, carbazole, fluorine, silole or cyclopentadiene are formed on the ladder-type multifused arenes to design and synthesize the hexacyclic, heptacyclic and nonacyclic units multifused arenes. For example, the present invention provides a method of synthesizing a monomer, including steps of providing a compound having a structure being one of Formula (I)

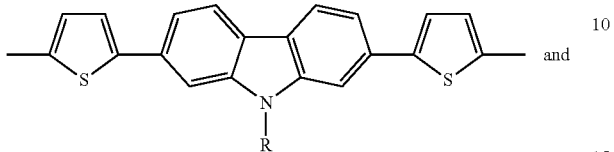

and

Formula (II)

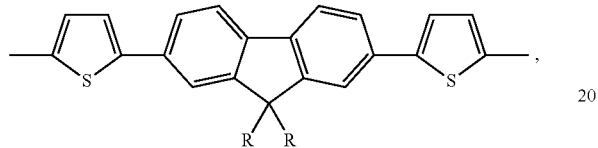

wherein R is a side chain at least including a carbon atom, and performing an annulation with the compound to cause the compound to form the monomer.

Besides, the present invention also links the conjugated small molecules of the ladder-type multifused arenes and that of the various electron deficient monomer/electron acceptor to form a p-type conjugated polymer. For example, the present invention also provides a method of synthesizing a p-type conjugated polymer, including steps of providing a compound having a structure being one of Formula (I)

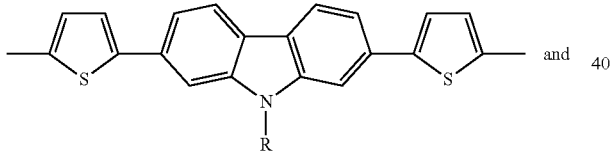

and

Formula (II)

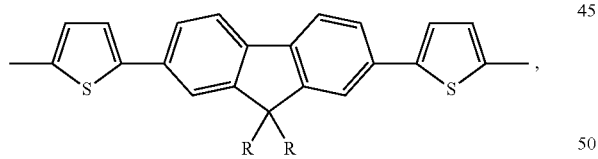

wherein R is a side chain at least including a carbon atom, forming at least one aromatic ring on the compound for form a monomer, and polymerizing the monomer and an electron acceptor to form the p-type conjugated polymer.

Further, the above electron acceptor/electron deficient monomer is one selected from a group consisting of:

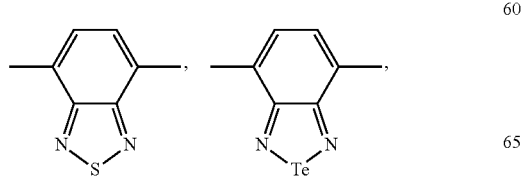

-continued

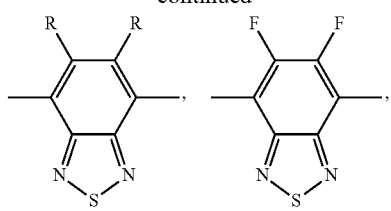

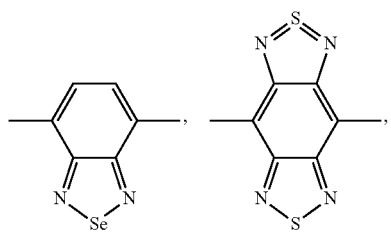

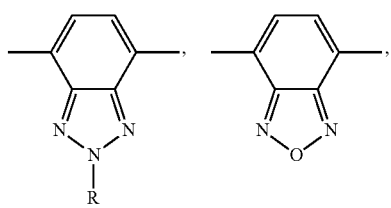

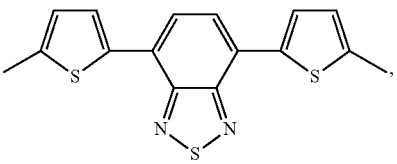

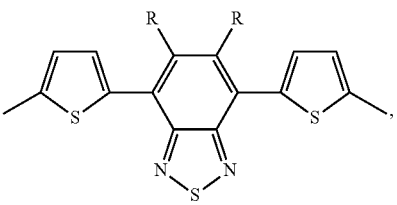

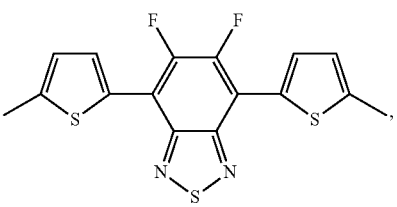

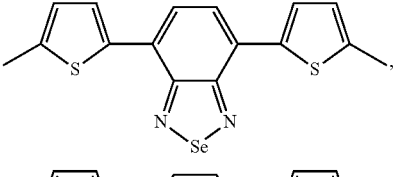

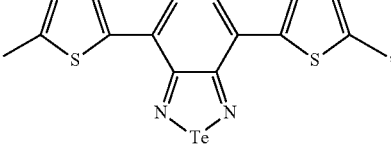

-continued
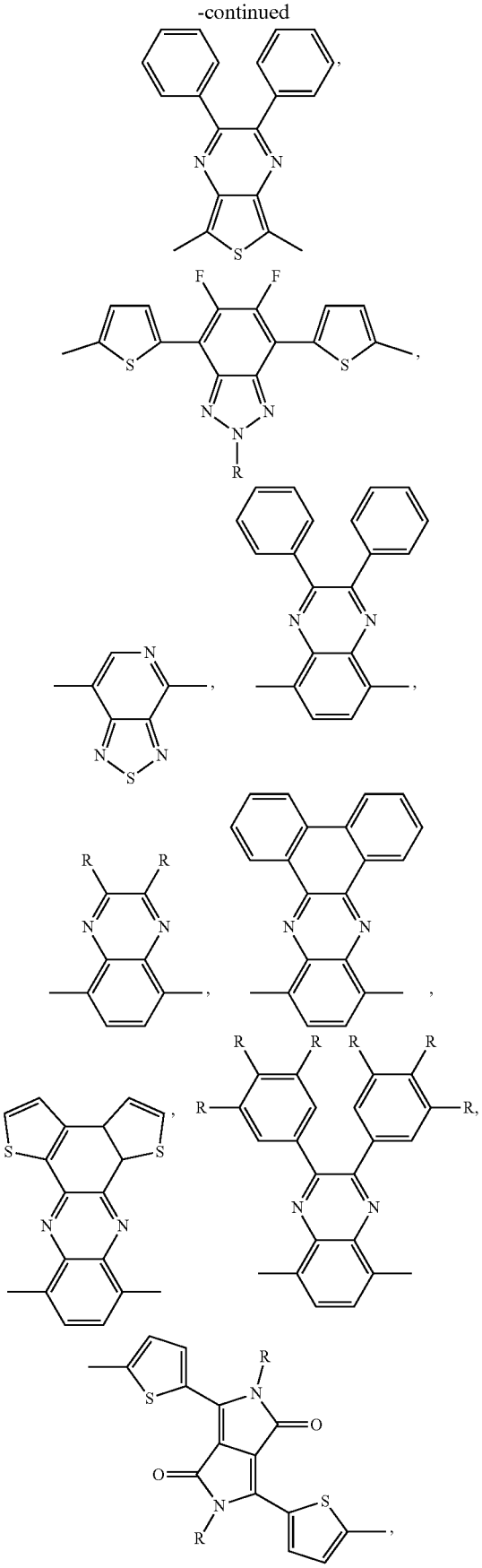
-continued
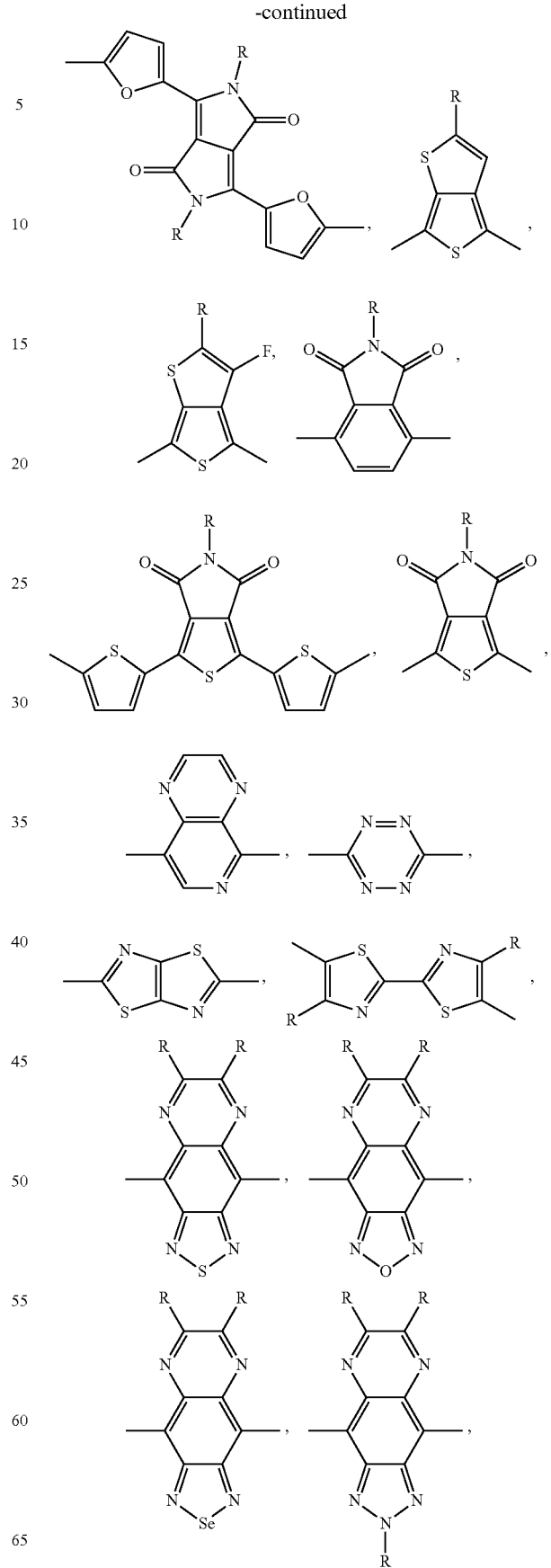

-continued

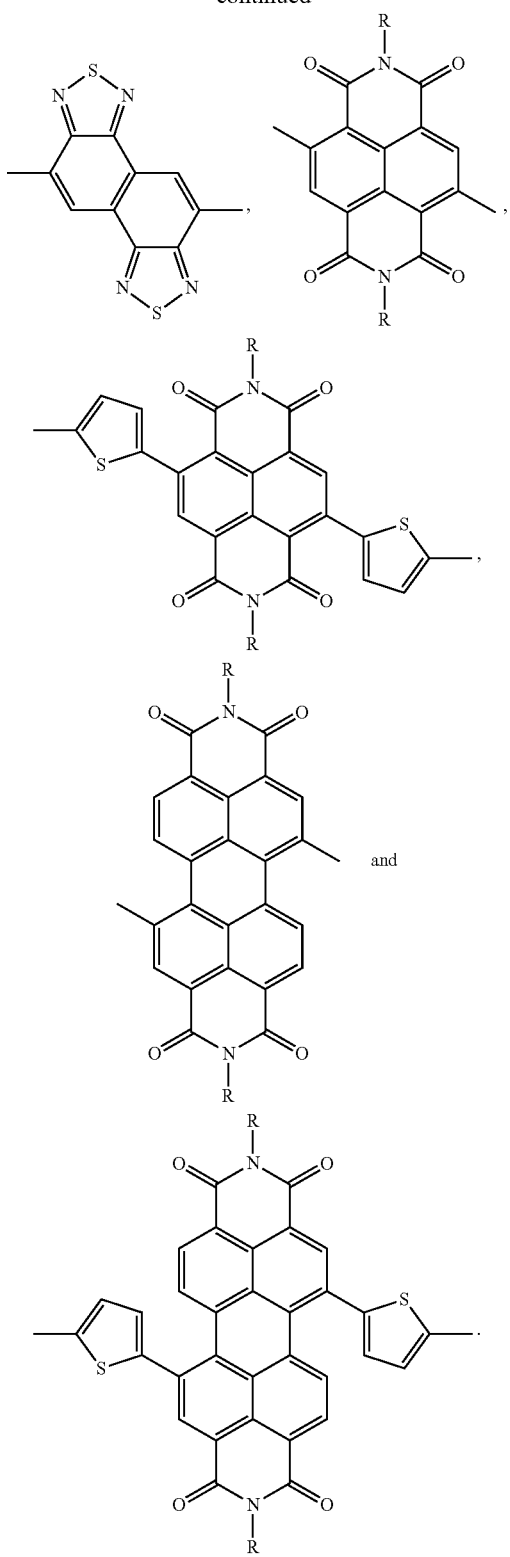

For example, the p-type conjugated polymer is preferably synthesized as a method including the steps of providing a compound

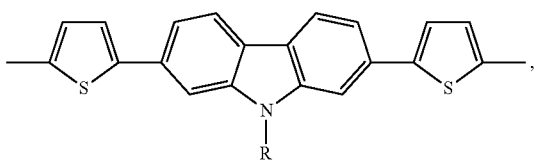

linking the thiophenes on both sides to the tricyclic system by a silicon atom respectively, modifying with an appropriate R group and providing a electron acceptor

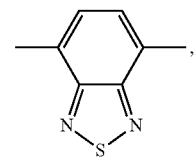

After polymerization, a ladder type heptacyclic multifused p-type conjugated polymer with a novel structure

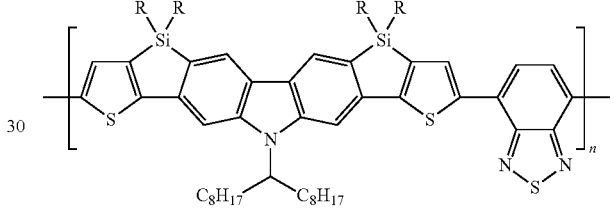

is formed, which maintains the same conjugated backbone but has an enhanced molecular planarity. It is proved that this ladder type heptacyclic multifused p-type conjugated polymer has a good optical absorption and electron hole transporting properties.

The side chain R in the above embodiments preferably has any length and size. Specifically, the side chain having at least one carbon atom is preferably be used in the side chain R as described in the present invention.

The p-type conjugated polymers is preferably blended with the n-type material such as $C_{70}$ derivative [6,6]-phenyl $C_{71}$-butyric acid methyl ester ($PC_{71}BM$) or $C_{60}$ derivative [6,6]-phenyl $C_{61}$-butyric acid methyl ester ($PC_{61}BM$) in various organic solvents and then spin-coated to serve as the active layer of the organic doped solar cell for achieving a high efficiency organic solar cell with a multi-layer structure.

The following Table 1 illustrates the respective optoelectronic properties of the elements in the active layer of the organic solar cell made by several p-type conjugated polymers of the present invention blending with $PC_{71}BM$.

TABLE 1

| Conjugated polymer | Blend ratio with $PC_{71}BM$ | Open circuit voltage (V) | Short circuit current (mA/cm$^2$) | Fill factor (%) | Power conversion efficiency (PCE, %) |
|---|---|---|---|---|---|
| PDTSCBT | 1:3 | 0.82 | 11.1 | 56.7 | 5.2 |
| PDTPCBT | 1:2 | 0.50 | 10.5 | 49.9 | 2.6 |
| PDTBCDTBT | 1:1.5 | 0.78 | 11.4 | 65.6 | 5.9 |
| PDTCFBT | 1:3 | 0.83 | 12.6 | 66.8 | 7.0 |
| PBBCPDTTPD | 1:2.5 | 0.85 | 11.7 | 51.7 | 5.2 |
| PBBCPDTBT | 1:2.5 | 0.75 | 12.5 | 51.6 | 4.8 |

TABLE 1-continued

| Conjugated polymer | Blend ratio with PC$_{71}$BM | Open circuit voltage (V) | Short circuit current (mA/cm$^2$) | Fill factor (%) | Power conversion efficiency (PCE, %) |
|---|---|---|---|---|---|
| PBBCPDTBT-F | 1:2.5 | 0.85 | 11.9 | 56.9 | 5.8 |
| PIDTTBT | 1:4 | 0.82 | 10.5 | 46.0 | 4.0 |
| PIDTTDTBT | 1:4 | 0.82 | 8.9 | 49.0 | 3.6 |
| PDITTDTBT | 1:4 | 0.92 | 10.7 | 58.4 | 5.8 |
| PDITTBT | 1:4 | 0.88 | 7.5 | 41.4 | 2.7 |
| PTPTPTBT | 1:4 | 0.76 | 11.4 | 61.0 | 5.3 |

Through the Table 1, it is known that the active layer elements made of the p-type conjugated polymers of the present invention blending with n-type material have good properties of high short circuit current and high PCE. Detailedly speaking, the multifused p-type conjugated polymer of the present invention is preferably applied to the organic blend solar cell having a multilayer structure, which is spin-coated on the PEDOT:PSS as an active layer by blending with the n-type material. The p-type material has the following properties. 1) It elongates effective conjugation length, 2) facilitates π-electron delocalization, 3) reduces the band gap, and 4) suppresses the rotational disorder around interannular single bounds to lower the reorganization energy and being beneficial for intrinsic charge mobility by the planar and rigid structure.

The present application enhances the scope and the intensity of the sunlight spectrum absorbed by the active layer by introducing a novel multifused p-type conjugated polymer into the active layer of the organic blend solar cell, and increases the hole transporting ability by the coplanar and rigid structure of the p-type conjugated polymer itself. Thereby, the short circuit current of the organic blend solar cell is enhanced and the re-combination probability of the electron hole is decreased to achieve a high efficiency organic solar cell with a multilayer structure.

Specifically, the present invention is further described by the following exemplary embodiments.

1. A polymer, having a structure being one selected from a group consisting of:

Formula (I)

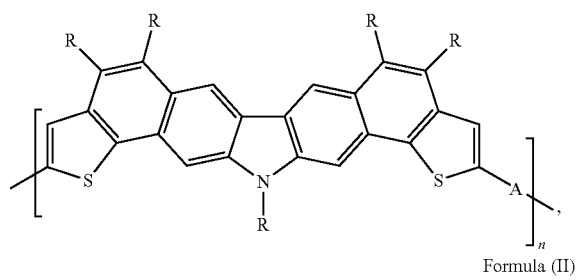

Formula (II)

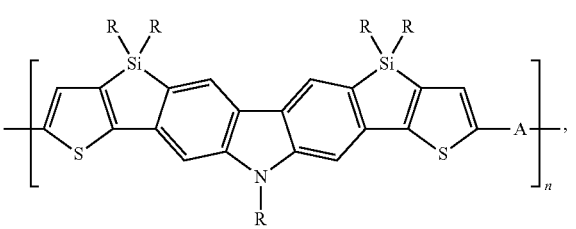

Formula (III)

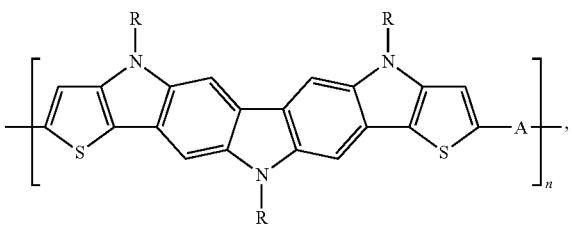

Formula (IV)

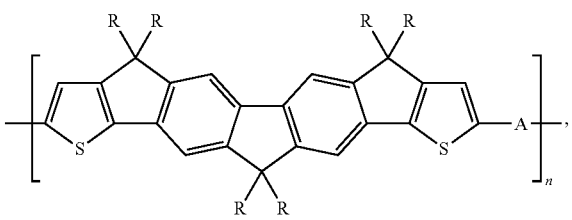

Formula (V)

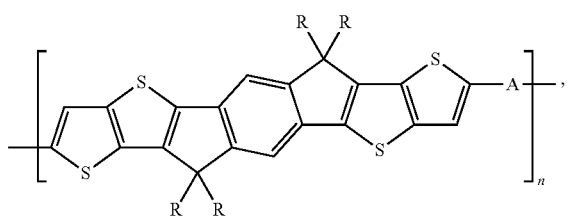

Formula (VI)

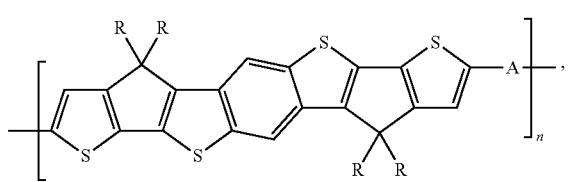

Formula (VII)

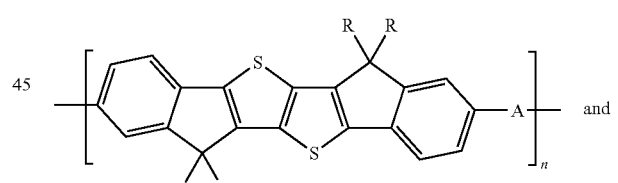

and

Formula (VIII)

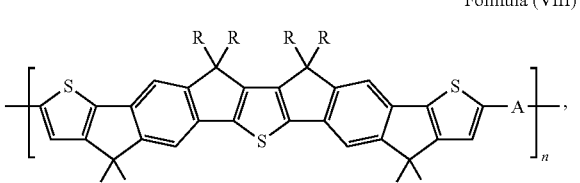

wherein A is an electron-deficient monomer, n is an integer larger than 2 and R is a side chain at least including a carbon atom.

2. According to example 1, wherein the electron-deficient monomer is one selected from a group consisting of

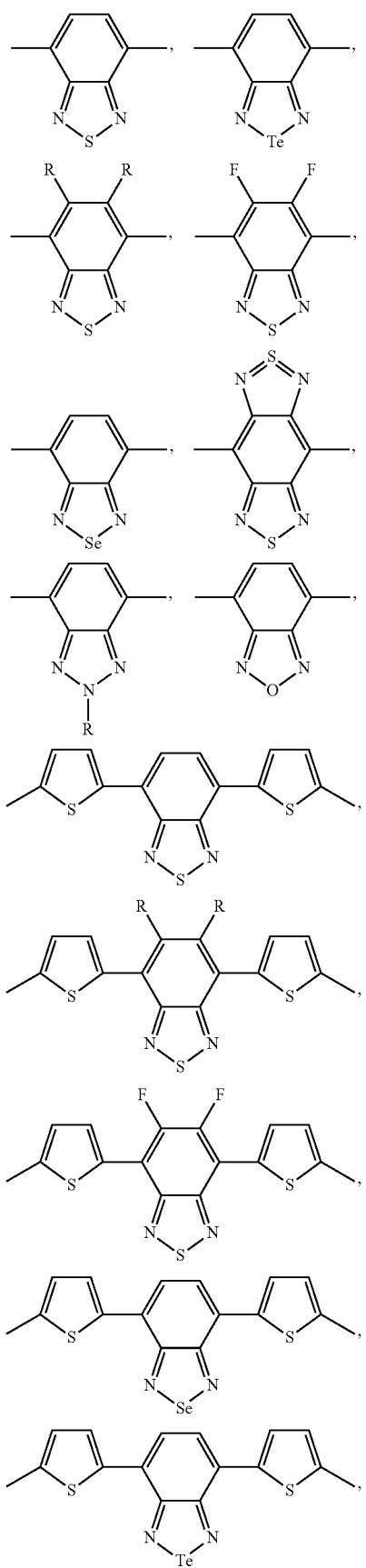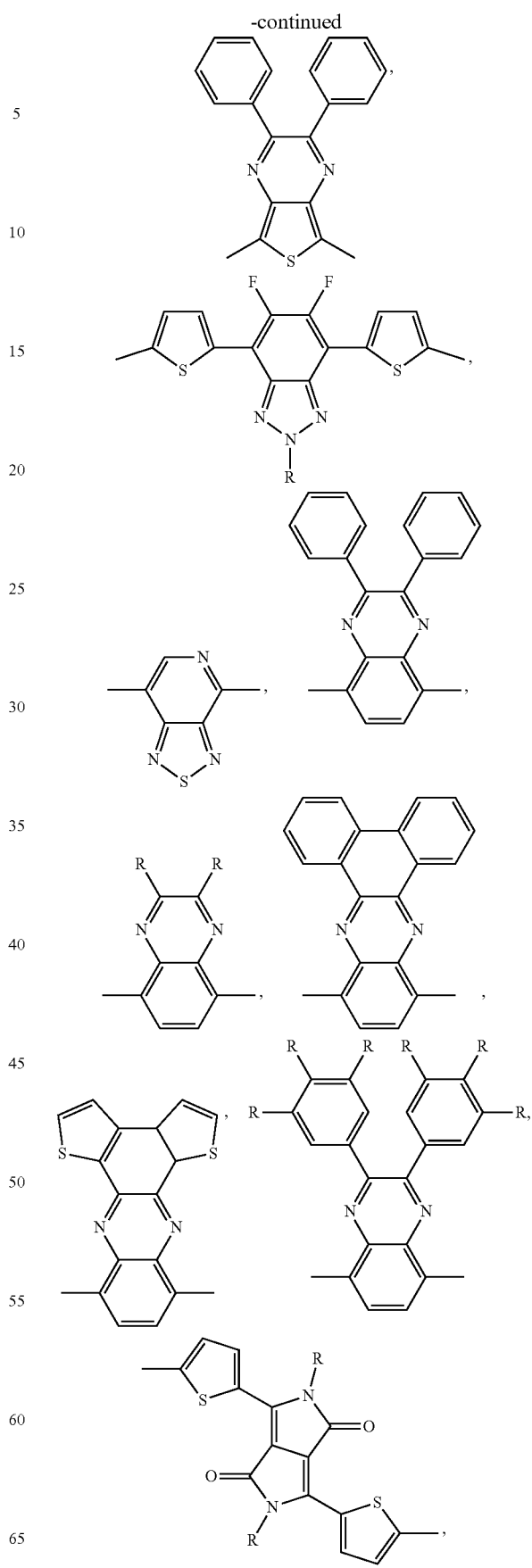
-continued

-continued
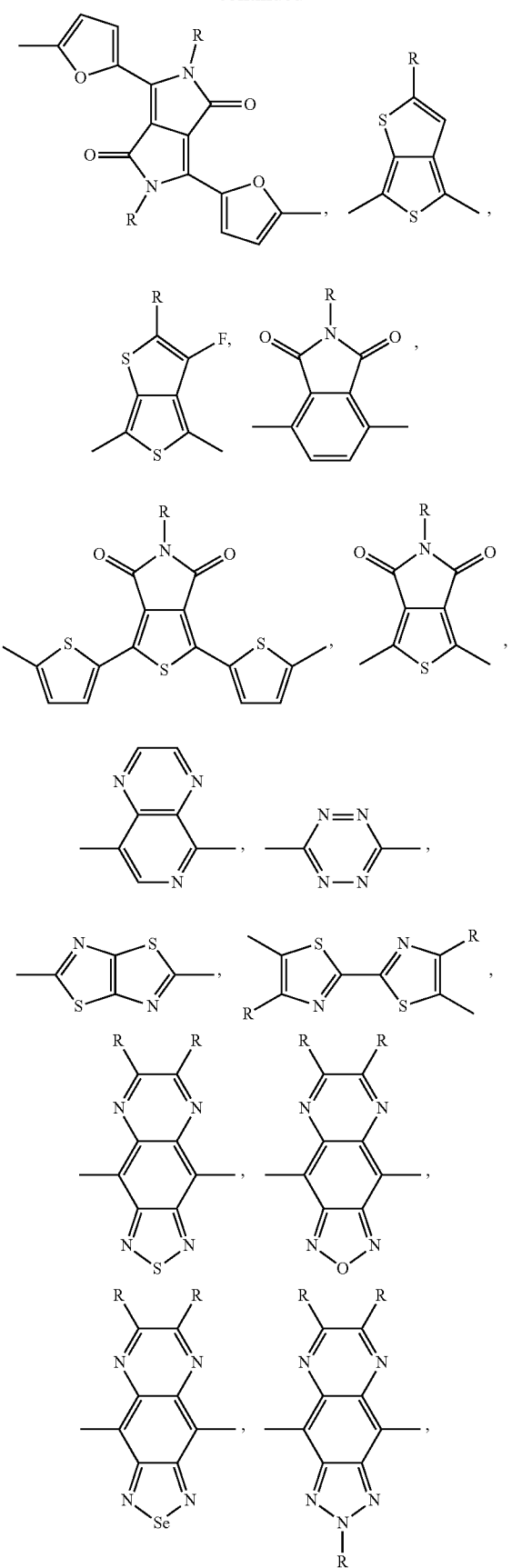
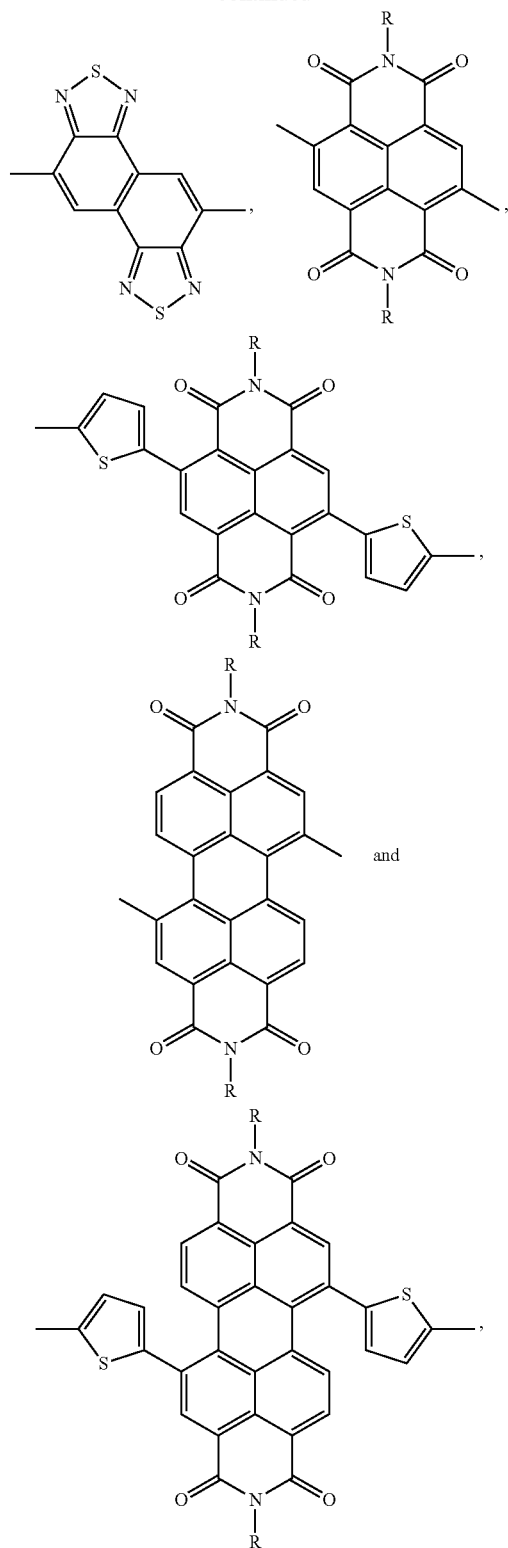
and R on the electron-deficient monomer is a side chain at least including a carbon atom.
3. A polymer material, comprising:
a plurality of monomers, wherein the plurality of monomers are one selected from a group consisting of Formula (I)

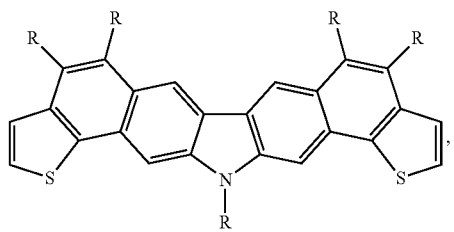

Formula (II)

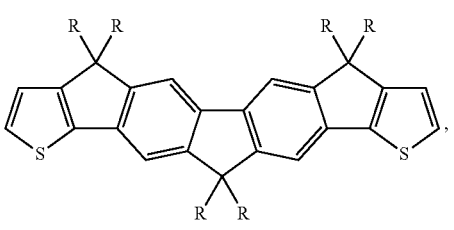

Formula (III)

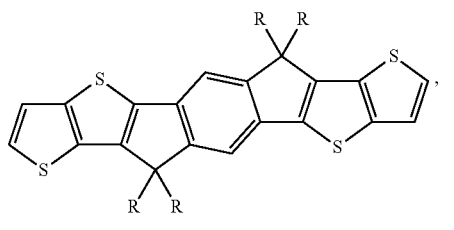

Formula (IV)

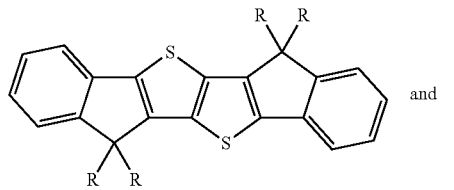

and

Formula (V)

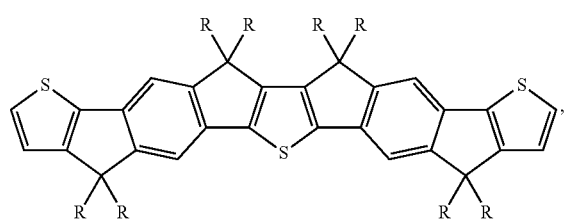

wherein R is a side chain at least including a carbon atom.

4. A polymer monomer having a structure being one selected from a group consisting of:

Formula (I)

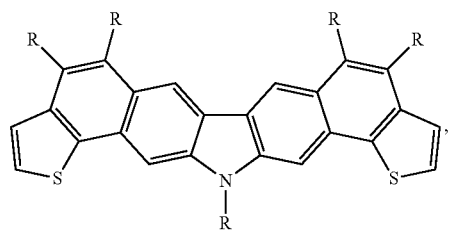

Formula (II)

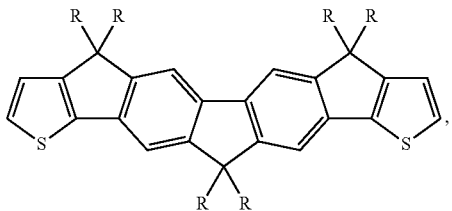

Formula (III)

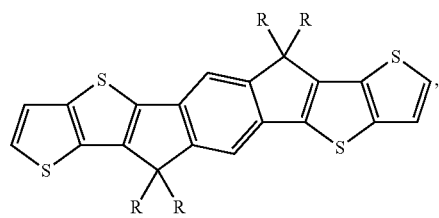

Formula (IV)

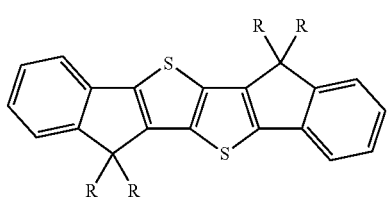

and

Formula (V)

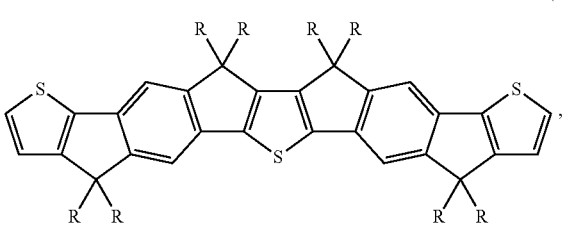

wherein R is a side chain at least including a carbon atom.

5. A method of synthesizing a monomer, including steps of:
providing a compound having a structure being one of Formula (I)

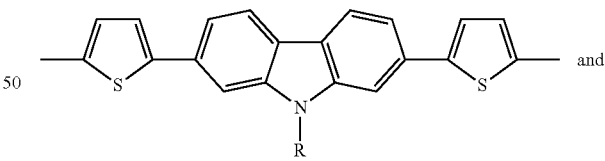

and

Formula (II)

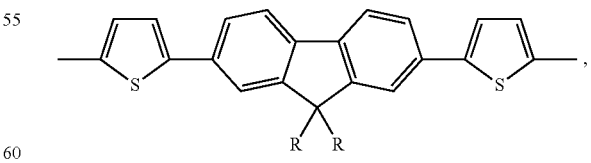

wherein R is a side chain at least including a carbon atom; and
performing an annulation with the compound to cause the compound to form the monomer.

6. According to example 5, wherein the annulation synthesizes at least one aromatic ring on the compound.

7. A method of synthesizing a polymer, including steps of:
providing a compound having a structure being one of

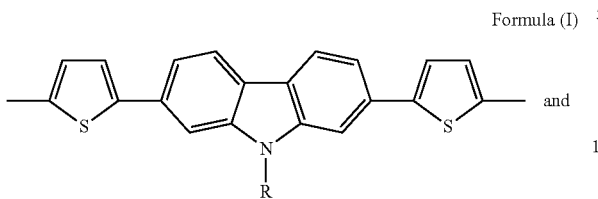

Formula (I)

and

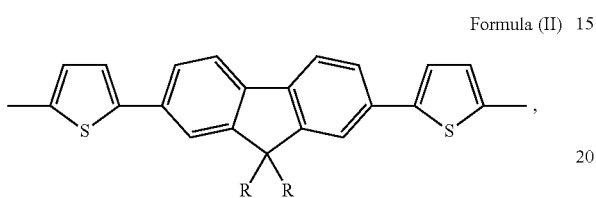

Formula (II)

, wherein R is a side chain at least including a carbon atom;

forming at least one aromatic ring on the compound to form a monomer; and polymerizing the monomer and an electron acceptor to form a polymer.

8. According to example 7, wherein the aromatic ring is a heterocycle.

9. A method of synthesizing a polymer, including steps of:

providing a monomer, wherein the monomer is one selected from a group consisting of:

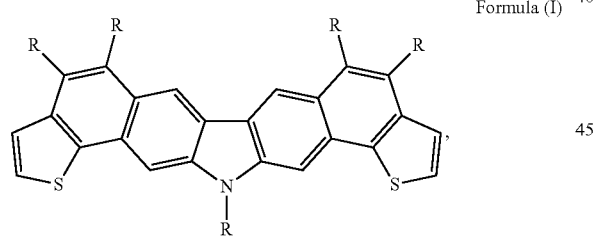

Formula (I)

,

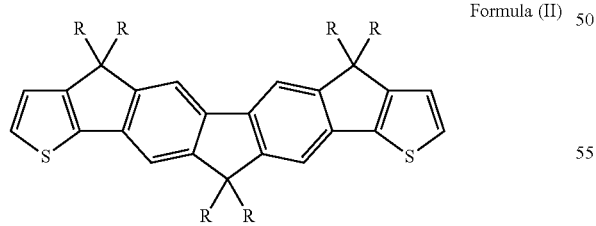

Formula (II)

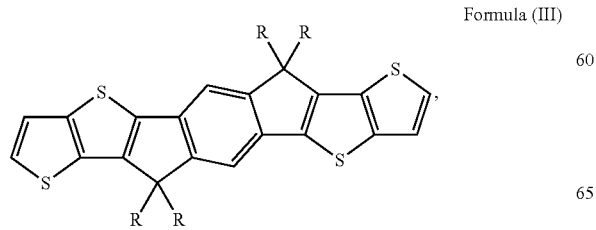

Formula (III)

,

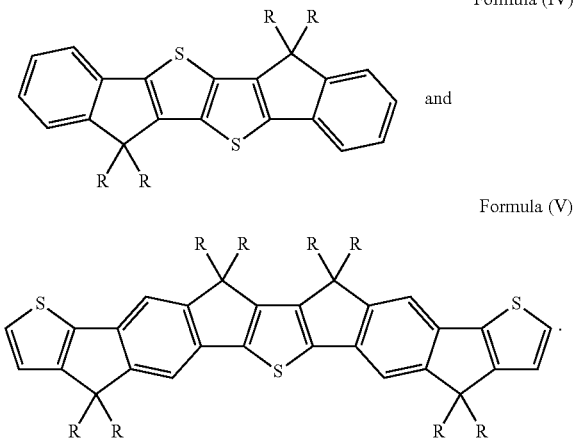

Formula (IV)

and

Formula (V)

.

10. According to example 9, wherein the electron acceptor is one selected from a group consisting of:

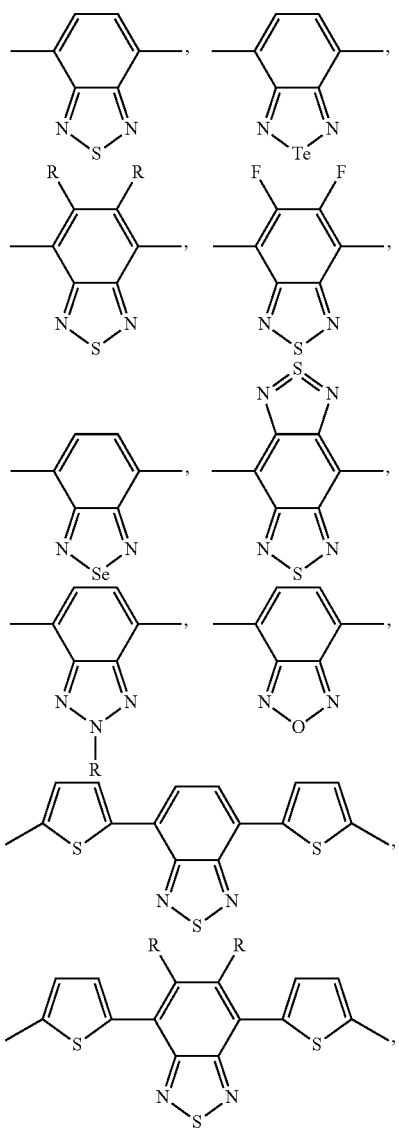

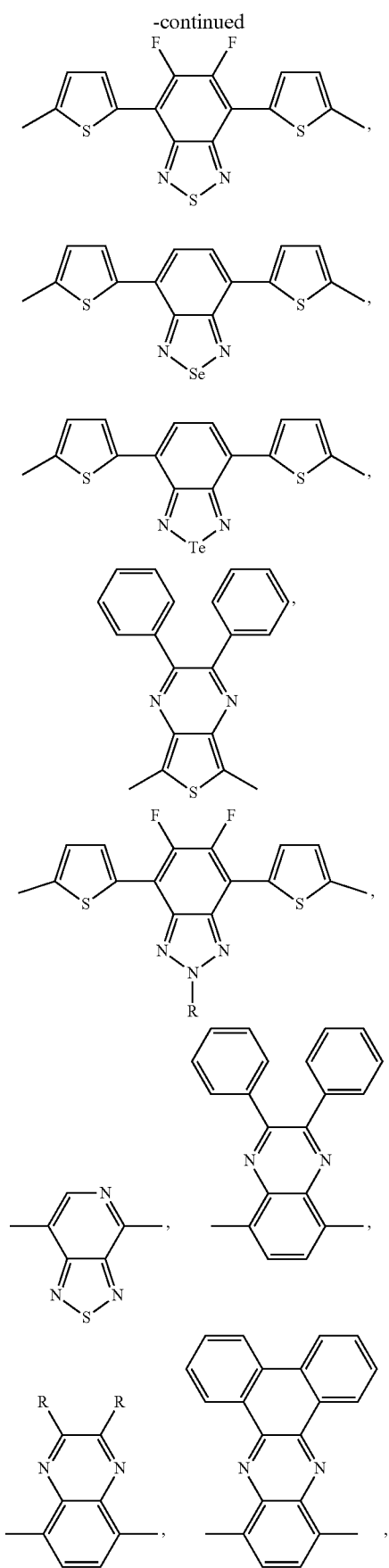
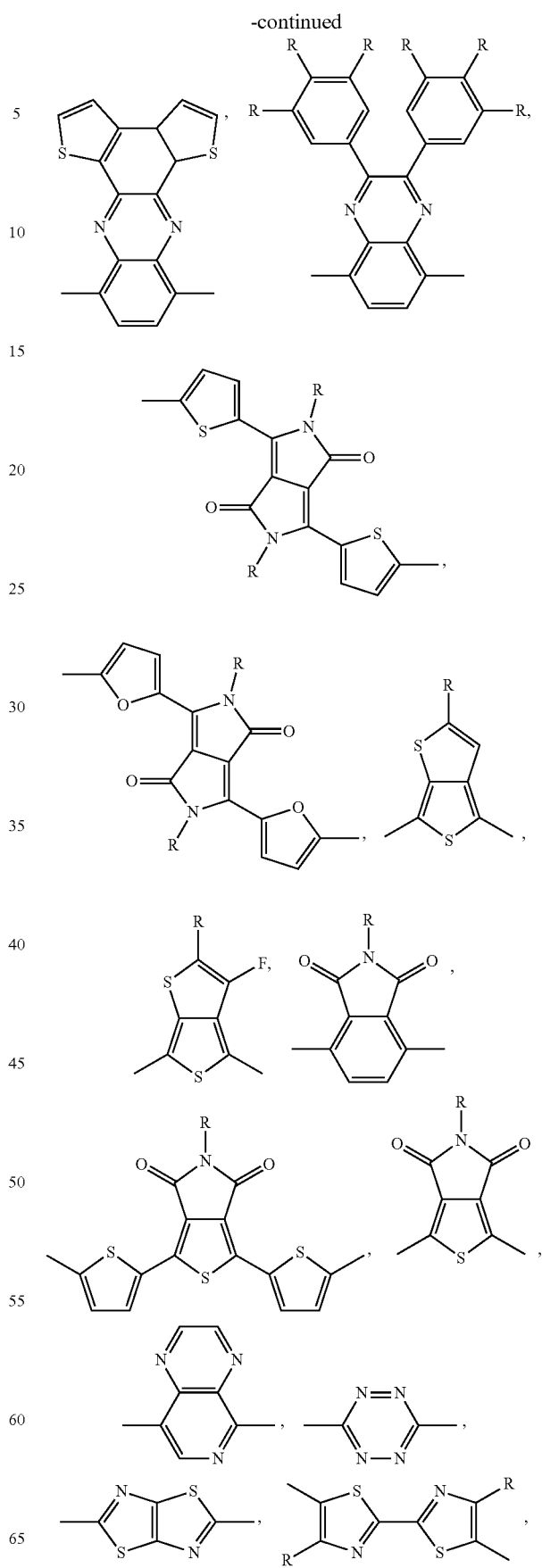

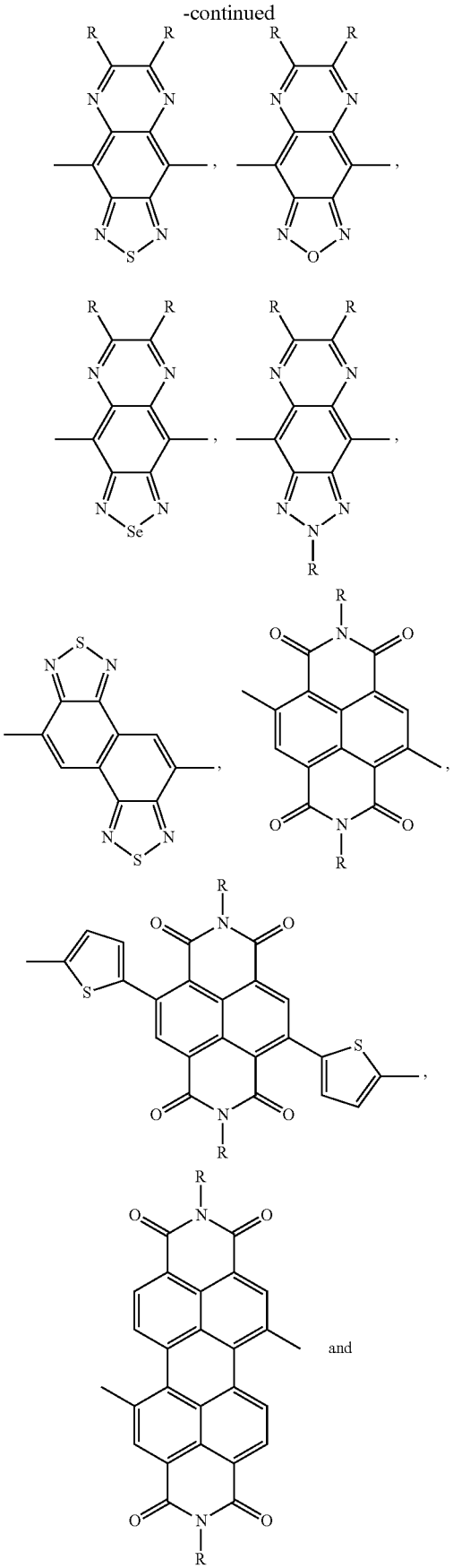

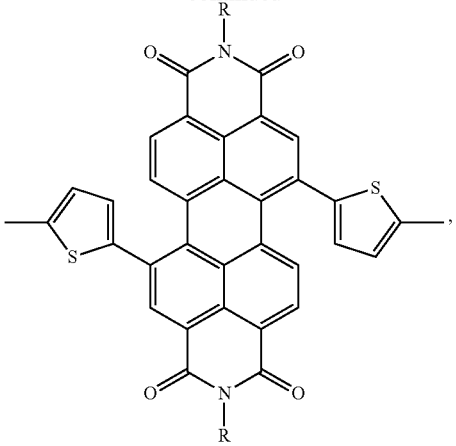

and R on the electron acceptor is a side chain at least including a carbon atom.

While the present invention has been detailedly described with reference to the above embodiments, it will be understood by those skilled in the art that various modifications and variations may be made therein without departing from the scope of the present invention as defined by the appended claims.

REFERENCES

1. Chiu-Hsiang Chen, Yen-Ju Cheng, Chih-Yu Chang, and Chain-Shu Hsu. Donor-Acceptor Random Copolymers Based on a Ladder-Type Nonacyclic Unit: Synthesis, Characterization, and Photovoltaic Applications. *Macromolecules.* 2011 44 (21), 8415-8424.
2. Yen-Ju Cheng, Chiu-Hsiang Chen, Yu-Shun Lin, Chih-Yu Chang, and Chain-Shu Hsu. Ladder-Type Nonacyclic Structure Consisting of Alternate Thiophene and Benzene Units for Efficient Conventional and Inverted Organic Photovoltaics. *Chemistry of Materials.* 2011 23 (22), 5068-5075.
3. Chih-Yu Chang, Yen-Ju Cheng, Shih-Hsiu Hung, Jhong-Sian Wu, Wei-Shun Kao, Chia-Hao Lee, Chain-Shu Hsu. Combination of Molecular, Morphological, and Interfacial Engineering to Achieve Highly Efficient and Stable Plastic Solar Cells. *Adv. Mater* 2012, 24, No. 04, 549-553.
4. Jhong-Sian Wu, Yen-Ju Cheng, Tai-Yen Lin, Chih-Yu Chang, Peng-I. Shih, and Chain-Shu Hsu. Dithienocarbazole-Based Ladder-Type Heptacyclic Arenes with Silicon, Carbon, and Nitrogen Bridges: Synthesis, Molecular Properties, Field-Effect Transistors, and Photovoltaic Applications. *Adv. Funct. Mater* 2012, 22(8), 1711-1722.
5. Yen-Ju Cheng, Sheng-Wen Cheng, Chih-Yu Chang, Wei-Shun Kao, Ming-Hung Liao and Chain-Shu Hsu. Diindenothieno[2,3-b]thiophene arene for efficient organic photovoltaics with an extra high open-circuit voltage of 1.14 ev. *Chem. Commun.*, 2012, 48, 3203-3205.

What is claimed is:

1. A method of synthesizing a polymer, comprising steps of:

providing a compound having a structure being one of

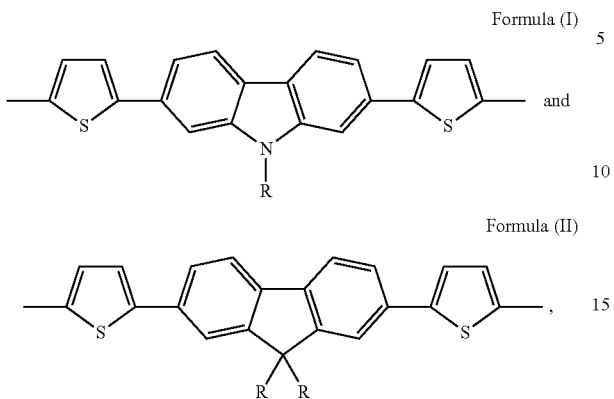

wherein R is a side chain at least comprising a carbon atom;

performing an annulation with the compound to cause the compound to form a monomer; and polymerizing the monomer and an electron acceptor to form the polymer.

2. A method as claimed in claim 1, wherein the electron acceptor is one selected from a group consisting of:

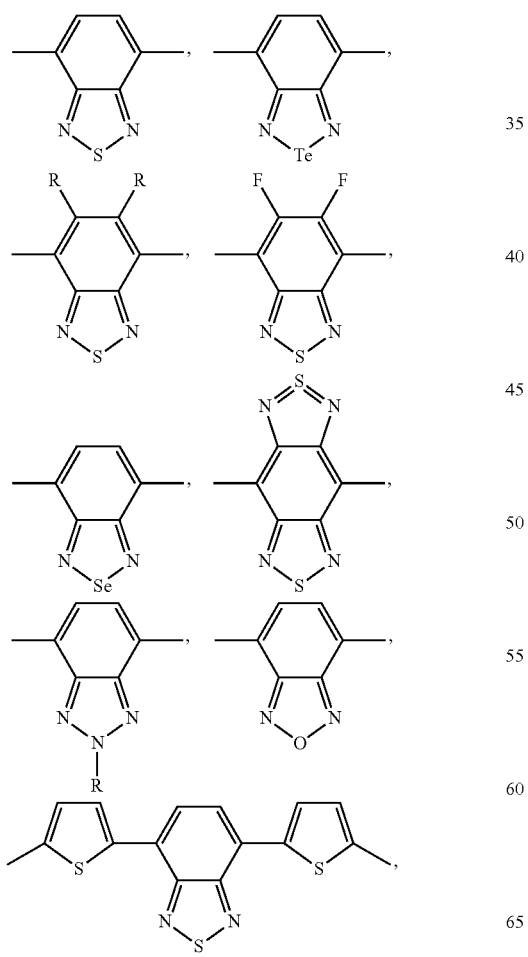

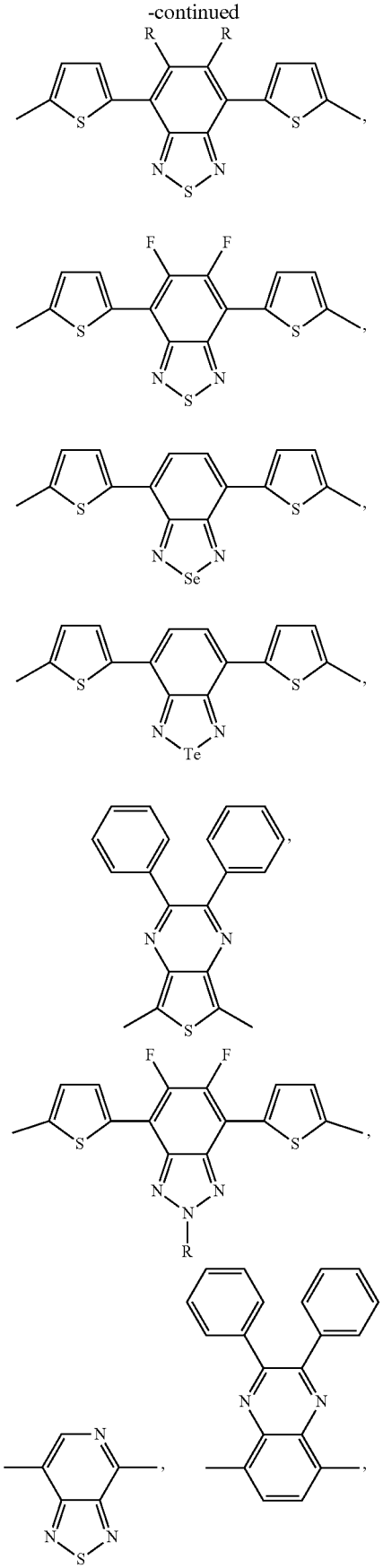

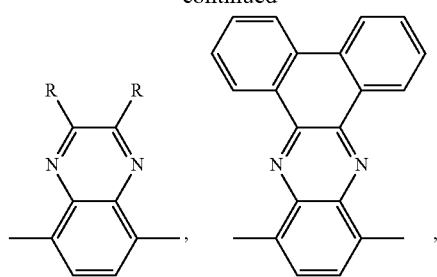
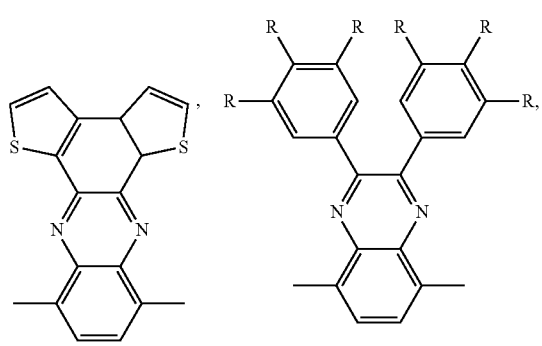
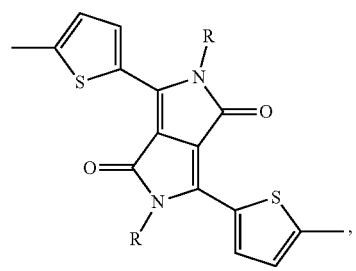
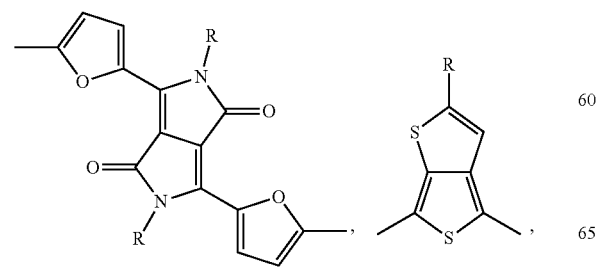
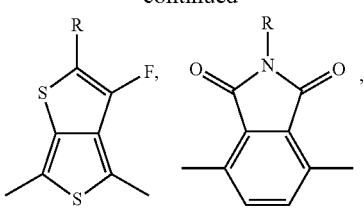
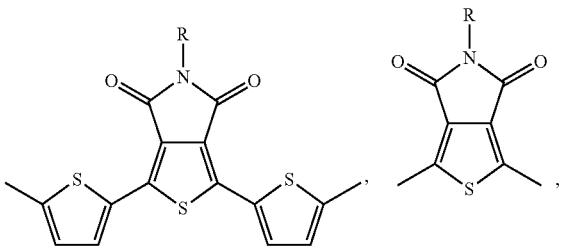
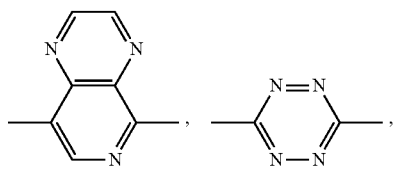
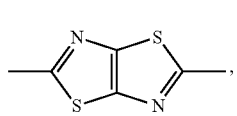
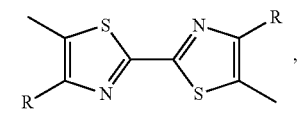
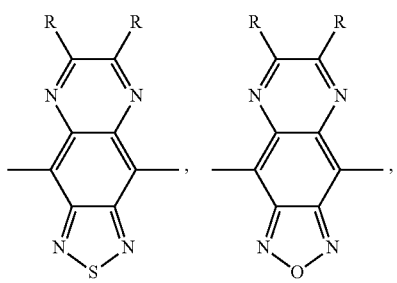
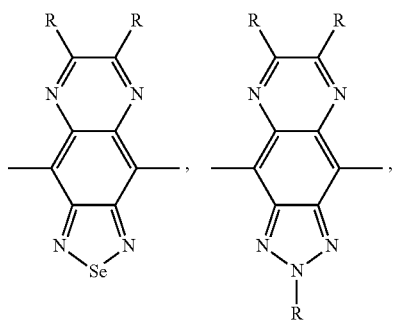

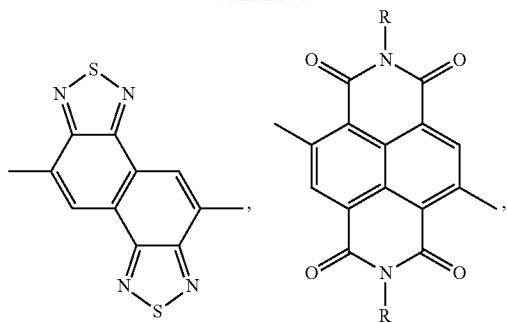
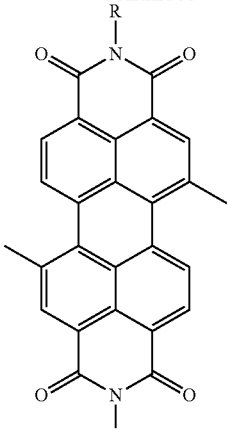
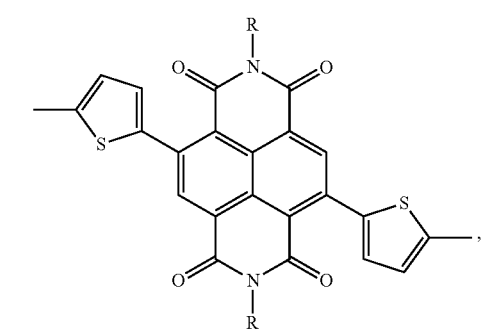
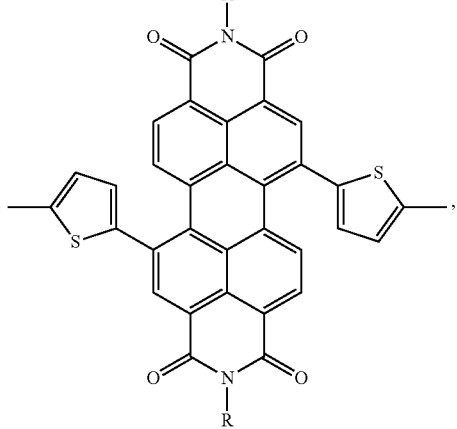
R on the electron acceptor is a side chain at least comprising a carbon atom.
* * * * *